US006863884B2

(12) United States Patent
Schauber et al.

(10) Patent No.: US 6,863,884 B2
(45) Date of Patent: Mar. 8, 2005

(54) PSEUDOTYPED RETROVIRAL VECTORS

(75) Inventors: Cherylene A. Schauber, San Francisco, CA (US); Christopher D. Pacheco, Ann Arbor, MI (US)

(73) Assignee: Cell Genesys, Inc., South San Francisco, CA (US)

( * ) Notice: Subject to any disclaimer, the term of this patent is extended or adjusted under 35 U.S.C. 154(b) by 0 days.

(21) Appl. No.: 10/425,324

(22) Filed: Apr. 29, 2003

(65) Prior Publication Data

US 2003/0207438 A1 Nov. 6, 2003

Related U.S. Application Data

(60) Provisional application No. 60/376,708, filed on May 1, 2002.

(51) Int. Cl.$^7$ .................. C12N 5/10; C12N 15/866; C12N 15/63; A61K 48/00
(52) U.S. Cl. ............... 424/93.2; 424/93.1; 424/93.6; 435/325; 435/366; 435/320.1; 435/455; 435/456
(58) Field of Search ............... 424/93.1, 93.2, 424/93.6; 435/325, 366, 320.1, 455, 456

(56) References Cited

U.S. PATENT DOCUMENTS

| | | | |
|---|---|---|---|
| 5,665,577 A | 9/1997 | Sodroski et al. | |
| 5,686,279 A | 11/1997 | Finer et al. | |
| 5,716,826 A | 2/1998 | Gruber et al. | |
| 5,739,018 A | 4/1998 | Miyanohara et al. | |
| 5,750,383 A | 5/1998 | Blissard et al. | |
| 6,013,516 A | 1/2000 | Verma et al. | |
| 6,338,953 B1 | 1/2002 | Boyce et al. | |

FOREIGN PATENT DOCUMENTS

WO    WO 99/09193    2/1999

OTHER PUBLICATIONS

Park et al., Biochem. Biophys. Res. Comm., 2001, vol. 289, pp. 444–450.*
Boyce, et al., Baculovirus–mediated gene transfer into mammalian cells, *Proc. Natl. Acad. Sci.*, USA, vol. 93, pp. 2348–2352, Mar. 1996, Genetics.
Chang, et al., Efficacy and safety analyses of a recombinant human immunodeficiency virus type 1 derived vector system, *Gene Therapy* (1999) 6:715–728.
Condreay et al., Transient and stable gene expression in mammalian cells transduced with a recombinant baculovirus vector, *Proc. Natl. Acad. Sci.*, USA, vol. 96, Jan. 1999, pp. 127–132, Cell Biology.
Farson et al., Large–Scale Manufacturing of Safe and Efficient Retrovirus Packaging Lines for Use in Immunotherapy Protocols, *The Journal Of Gene Medicine* (1999) 1:195–209.
Farson et al., A New–Generation Stable Inducible Packaging Cell Line for Lentiviral Vectors, *Human Gene Therapy*, 12:981–997, May 20, 2001.

Gasmi, et al., Requirements for Efficient Production and Transduction of Human Immunodeficiency Virus Type 1–Based Vectors, *Journal Of Virology*, Mar. 1999, pp. 1828–1834.
Hofmann, et al., Efficient gene transfer into human hepatocytes by baculovirus vectors, *Proc. Natl. Acad. Sci USA*, vol. 92, pp. 10099–10103, Oct. 1995, Cell Biology.
Klages, et al., A Stable System for the High–Titer Production of Multiply Attenuated Lentiviral Vectors, *Molecular Therapy*, vol. 2, No. 2, Aug. 2000, pp. 170–176.
Klimatcheva, et al., Lentiviral Vectors and Gene Therapy, *Frontiers in Bioscience* Jun. 1, 1999; 4:D481–496.
Monsma et al., Identification of a Membrane Fusion Domain and an Oligomerization Domain in the Baculovirus GP64 Envelope Fusion Protein, *Journal of Virology*, Apr. 1995, p. 2583–2595.
Sandig, et al., Gene Transfer into Hepatocytes and Human Liver Tissue by Baculovirus Vectors, *Human Gene Therapy* 7:1937–1945, Oct. 20, 1996.
Zufferey, et al., Multiply attenuated lentiviral vector achieves efficient gene delivery in vivo, *Nature Biotechnology*, vol. 15, Sep. 1997, pp. 871–875.
Product description: PacPAK6 DNA, Clontech Laboratories, Palo, Alto, CA, pp. 1–4.
Blissard, et al., Location, Sequence, Transcriptional Mapping, and Temporal Expression of the g64 Envelope Glycoprotein Gene of the *Orgyia pseudotsugata* Multicapsid Nuclear Polyhedrosis Virus, *Virology* 170, pp. 537–555 (1989).
Burns et al., Proc. Natl. Acad. Sci. USA (1993) 90:8033–8037.
DePolo et al., Mol. Ther. (2000) 2:218–222.
Dull et al., J. Virology (1998) 72(11):8463–8471.
Emi et al., J. Virol. (1991) 65:1202–1207.
Huser et al., Nat. Biotechnol. (2001) 19:451–455.
Hofmann et al., Gene Ther. (1998) 5:531–536.
Kafri et al., J. Virol (1999) 73:576–584.
Kavanaugh et al., Proc. Natl. Acad. Sci. USA (1994) 91:7071–7075.
Kumar et al., Hum. Gene. Ther. (2003) 14:67–77.
Menoret et al., Hum. Gene. Ther. (2002) 13:1383–1390.
Ory et al., Proc. Natl. Acad. Sci. USA (1996) 93:11400–11406.

(List continued on next page.)

*Primary Examiner*—David Guzo
(74) *Attorney, Agent, or Firm*—Linda R. Judge; Gates & Cooper LLP

(57) ABSTRACT

The present invention provides pseudotyped retroviral vectors and packaging systems and methods of using such vectors for retroviral-mediated gene transfer. In particular, the present invention provides a retroviral packaging system that comprises at least two vectors: a first vector comprising a gag, a pol, or gag and pol genes; and a second vector comprising a functionally modified or heterologous envelope gene, for example, a baculovirus envelope gene.

26 Claims, 7 Drawing Sheets

OTHER PUBLICATIONS

Sandrin et al., Blood (2002) 100:823–832.
Sarkis et al., Proc. Natl. Acad. Sci. USA (2000) 97:14638–14643.
Takeuchi et al., Nature (1996) 379:85–88.
Takeuchi et al., J. Virol. (1997) 71:6174–6178.
Tani et al., Virology (2001) 279:343–353.
Welsh et al., Nature (1975) 257:612–614.
Xu et al., Mol. Ther. (2002) 5:141–153.
Yee et al., Methods Cell Biol. (1994) 43:99–112.
Zufferey et al., J. Virology (1998) 72(12):9873–9880.

* cited by examiner

SEQUENCE LISTING

<160> NUMBER OF SEQ ID NOS: 2

<210> SEQ ID NO 1
<211> LENGTH: 48
<212> TYPE: DNA
<213> ORGANISM: Artificial Sequence
<220> FEATURE:
<223> OTHER INFORMATION: primer

<400> SEQUENCE: 1
acctgggaat tcgccgccac catgctacta gtaaatcagt cacaccaa            48

<210> SEQ ID NO 2
<211> LENGTH: 37
<212> TYPE: DNA
<213> ORGANISM: Artificial Sequence
<220> FEATURE:
<223> OTHER INFORMATION: primer

<400> SEQUENCE: 2
actgacgaat tcttaatatt gtctattacg gtttcta                        37

PSEUDOTYPED RETROVIRAL VECTORS

This application claims priority to U.S. provisional application No. 60/376,708, filed May 1, 2002, the entire contents of which are incorporated herein by reference.

TECHNICAL FIELD OF THE INVENTION

The present invention relates to retroviral vectors and their use in gene therapy. In particular it relates to pseudotyped retroviral vectors. The invention provides novel retroviral packaging vectors, stable packaging cell lines, stable producer cell lines, recombinant retroviruses carrying a foreign gene of interest and methods relating to the use thereof, as well as methods for producing recombinant retrovirus in mammalian cells.

BACKGROUND OF THE INVENTION

Retroviral vectors are a common tool for gene delivery (Miller, 1992, Nature 357: 455–460). The biology of retroviral proliferation enables such a use. Typically, wild type full length retroviral mRNA's serve both as a template for synthesis of viral proteins and as the viral genome. Such mRNA's encompass a region called the encapsidation signal which binds certain viral proteins thereby ensuring specific association of that mRNA with the produced virions. On infection of the target cell, reverse transcription of the retroviral mRNA into double stranded proviral DNA occurs. The retroviral enzyme, integrase, then binds to both long terminal repeats (LTR) which flank the proviral DNA and subsequently catalyzes the integration thereof into the genomic DNA of the target cell. Integrated proviral DNA serves as the template for generation of new full-length retroviral mRNA's.

Retroviral vectors have been tested and found to be suitable delivery vehicles for the stable introduction of a variety of genes of interest into the genomic DNA of a broad range of target cells. The ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, the types of cells that a retrovirus can infect can be altered using pseudotyped retroviral vectors in which the encoded native envelope protein is replaced by a heterologous envelope protein that has a different cellular specificity than the native envelope protein (e.g., binds to a different cell-surface receptor as compared to the native envelope protein). The ability to direct the delivery of retroviral vectors encoding a transgene to a specific type of target cells is highly desirable for gene therapy applications.

The G glycoprotein from vesicular stomatitis virus (VSV-G) has been used extensively for pseudotyping retroviral vectors, including lentiviral vectors (see e.g., Emi et al., J. Virol. (1991) 65:1202–1207; Burns et al., Proc. Natl. Acad. Sci. USA (1993) 90:8033–8037). VSV-G has been used in gene transfer protocols because of its broad species and tissue tropism and its ability to confer physical stability and high infectivity to vector particles (Yee et al, Methods Cell Biol. (1994) 43:99–112). However, the high fusogenicity of VSV-G causes rapid syncytia formation and cell death, making it difficult to generate stable cell lines expressing the protein (see e.g., Ory et al., Proc. Natl. Acad. Sci. USA (1996) 93:11400–11406). A number of groups have generated stable packaging and producer cell lines using VSV-G, but in all cases a repressible or inducible promoter regulates the expression of VSV-G (see e.g., Ory et al., Proc. Natl. Acad. Sci. USA (1996) 93:11400–11406; Farson et al., Hum. Gene Ther. (2001) 12:981–997; Kafri et al., J. Virol. (1999) 73:576–584). While regulated expression can potentially avoid the problem of VSV-G cytotoxicity, it makes stable production of viral vectors more complicated and impractical, and cell line generation more time-consuming.

Further, the broad tissue tropism of VSV-G can be disadvantageous in gene therapy applications because in some in vivo gene applications, it may be important to restrict the transfer and expression of a transgene to specific cell types. However, the broad distribution of the VSV-G receptor precludes this type of targeted transduction, even in instances of directed injection. VSV-G pseudotypes may transduce target cells of interest but following systemic administration may also transduce other cell types, thus, making it be problematic for use in gene therapy protocols. Antigen presenting cells (APC's), for instance, are cells that could cause deleterious immune responses if they are inadvertently transduced. Further, VSV-G pseudotyped lentiviral vectors can efficiently transduce APC's from mice and humans and can elicit immune responses against the transgene product thus negating the therapeutic effects of the expressed product (see e.g., Dyall et al, Blood (2001) 97:114–121; Chinnasamy et al, Hum. Gene Ther. (2000) 11:1901–1909; Metharom et al., Hum. Gene Ther. (2001) 12:2203–2213; VandenDriessche et al, Blood (2002) 100:813–822).

Systemic administration of viral vectors also exposes the vector particles to possible inactivation by serum complement (see e.g., Welsh et al., Nature (1975) 257:612–614). Complement inactivation of vectors is dependent on the species derivation of the cell line used to produce the vectors as well as the identity of the envelope glycoprotein used for pseudotyping (see e.g., Takeuchi et al., Nature (1996) 379:85–88; Takeuchi et al., J. Virol. (1 997) 71:6174–6178). VSV-G pseudotypes, regardless of producer cell type, will be inactivated by human serum complement while vectors pseudotyped with other envelope glycoproteins such as the MLV amphotropic envelope (Ampho) or RD114 are resistant to inactivation (DePolo et al., Mol. Ther. (2000) 2:218–222; Sandrin et al., Blood (2002) 100:823–832).

Thus, the use of VSV-G to pseudotype retroviruses for gene therapy applications has been attractive because of its high infectious titer and physical stability. In addition, VSV-G has been attractive due to its broad tropism, making it suitable for use with a wide variety of target cell types, including human cells. Unfortunately, this broad tropism can result in transduction of cells in which expression of the transgene is not desired, such as antigen presenting cells (APCs). However, in addition to drawbacks related to transduction of APCs, VSV-G, when constitutively expressed, can be cytotoxic, inhibit vector production, and render the vector sensitive to complement inactivation.

Consequently, because of the many disadvantages of VSV-G, there is considerable need for alternative envelope glycoproteins that have more suitable properties for use with retroviral vectors, including lentiviral vectors, in gene transfer applications. Of particular advantage would be the identification of envelope proteins that confer selective tropism, high titer in vivo, reduced cytotoxicity, resistance to complement inactivation, and reduced ability to transduce APC's.

SUMMARY OF THE INVENTION

The invention disclosed herein offers advantages over conventional retroviral gene delivery systems through the unexpected pseudotyping of retroviruses with baculoviral envelope proteins in a surprisingly feasible and efficient system. The invention provides an alternative to pseudotyping retroviruses with VSV-G that offers broad tropism but lacks the cytotoxicity associated with VSV-G. The invention provides a retroviral packaging system that comprises at least two vectors: a first vector comprises a first nucleotide sequence comprising a gag, a pol, or gag and pol genes; and a second vector comprises a second nucleotide sequence comprising a heterologous or functionally modified envelope gene. Preferably, the heterologous or functionally modified envelope gene is a baculoviral envelope gene, e.g., a gp64 envelope gene. In a preferred embodiment, the retroviral elements are derived from a lentivirus, such as HIV. Preferably, the vectors lack a functional tat gene and/or functional accessory genes (vif, vpr, vpu, vpx, nef). In another preferred embodiment, the system further comprises a third nucleotide sequence that comprises a rev gene. The packaging system can be provided in the form of a packaging cell that contains the first, second, and, optionally, third nucleotide sequences.

The invention further provides a producer cell that comprises the packaging system of the invention and a retroviral transfer vector comprising a transgene. The producer cell of the invention is capable of producing a recombinant retrovirus pseudotyped with a heterologous or functionally modified envelope and carries a transgene. The recombinant retrovirus is capable of infecting a host cell, thereby delivering the transgene to the host cell for expression.

The invention additionally provides a method of delivering a transgene to a cell. The method comprises contacting the cell with a recombinant retroviral vector pseudotyped with a heterologous or functionally modified envelope protein produced by the producer cell of the invention. In one embodiment, the transgene is a therapeutic transgene. The cell can be in vivo, in vitro or ex vivo.

BRIEF DESCRIPTION OF THE FIGURES

FIG. 6a depicts PBS-injected; FIG. 6b depicts VSV-G vector injected; FIG. 6c depicts gp64-vector injected; and FIG. 6d Ampho-vector injected mouse liver.

DETAILED DESCRIPTION OF THE INVENTION

Figure 1:
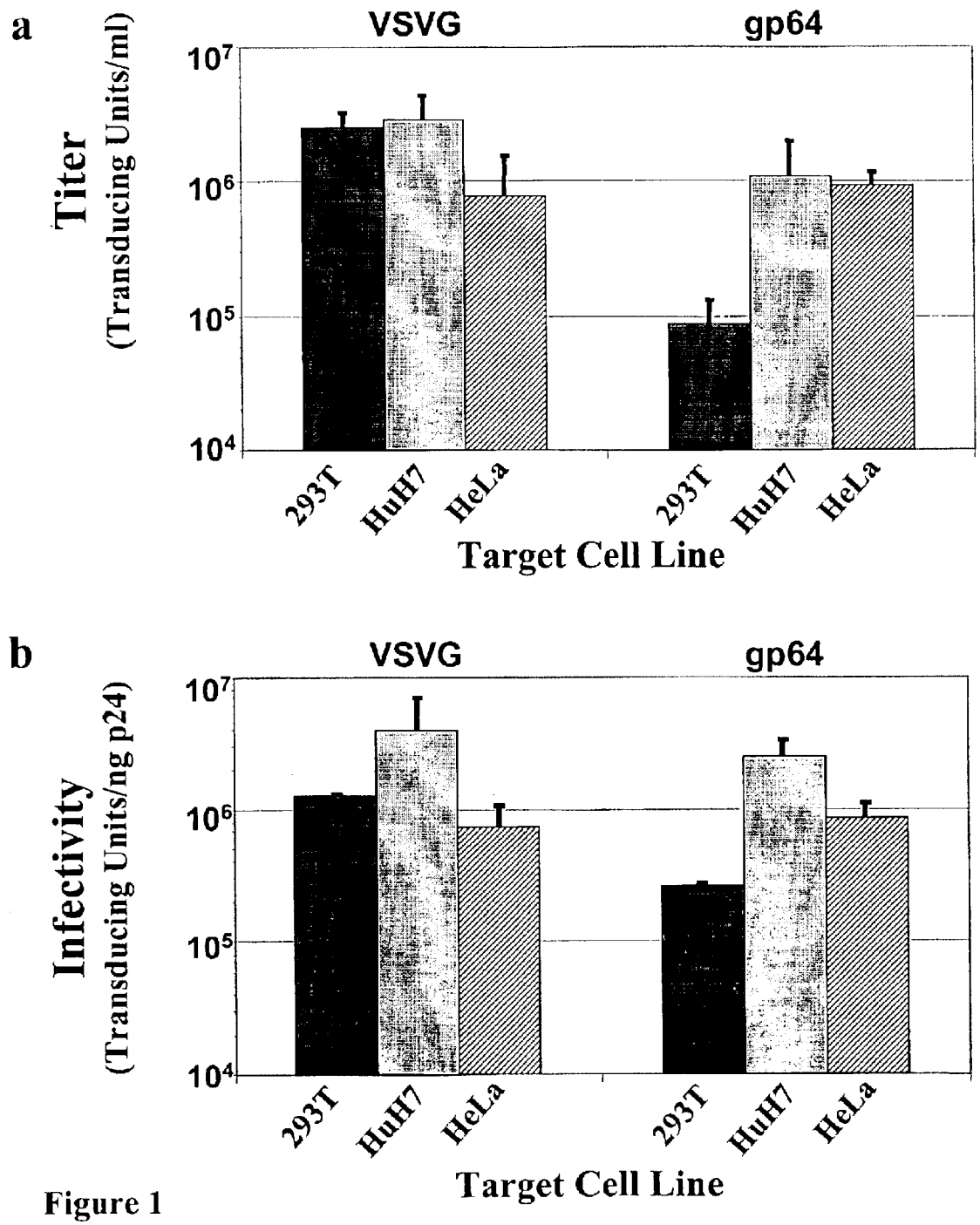
FIGS. 1a–b are bar graphs showing a titer and an infectivity comparison of VSV-G and gp64-pseudotyped lentiviral vectors on three cell lines. For the titer comparison depicted in FIG. 1a, the unconcentrated preparations of 3$^{rd}$ generation lentiviral vectors carrying a GFP transgene were produced by transient transfection and were pseudotyped with either the VSV-G (left) or gp64 (right) envelope glycoprotein. These preparations were assayed for endpoint titers on 293T (black bars; n=3), HuH7 human hepatoma (gray bars; n=5) and HeLa cells (hatched bars; n=2). The titer values (transducing units/ml) were calculated based on % GFP positive cells as determined by FACS analysis. The standard deviations of titers determined for independent vector preparations are shown as error bars. The infectivity values (transducing units/ng p24$^{Gag}$) of the preparations were calculated by dividing the titer values in transducing units/ml (depicted in FIG. 1a) by the p24$^{Gag}$ concentrations in ng/ml. For the infectivity comparison depicted in FIG. 1b, p24$^{Gag}$ concentrations in ng/ml were determined by ELISA, in order to normalize the transducing units to total particles in the lentiviral vector preparations.

The present invention is based on the discovery that retroviral vectors can be pseudotyped with a baculovirus envelope protein and that the resulting recombinant vectors can be used to achieve production of recombinant retroviral particles that gain entry into mammalian cells. Recombinant retroviral particles pseudotyped with baculoviral envelope protein in accordance with the invention have been demonstrated to achieve high titers, comparable to those achieved using the VSV-G protein or the MLV amphotropic envelope. The invention thereby provides a gene therapy tool that offers enhanced efficiency through tissue-specific infectivity as well as reduced cytotoxicity and immunogenicity.

Definitions

All scientific and technical terms used in this application have meanings commonly used in the art unless otherwise specified. As used in this application, the following words or phrases have the meanings specified.

As used herein, "a" or "an" means at least one, unless clearly indicated otherwise.

As used herein, "nucleotide sequence", "nucleic acid sequence", "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Nucleic acid sequences can be, e.g., prokaryotic sequences, eukaryotic mRNA sequences, cDNA sequences from eukaryotic mRNA, genomic DNA sequences from eukaryotic DNA (e.g., mammalian DNA), and synthetic DNA or RNA sequences, but are not limited thereto.

As used herein, a "promoter" refers to a nucleic acid sequence capable of directing transcription.

As used herein, "expression control sequence" refers to a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, a "retroviral transfer vector" refers to the expression vector that comprises a nucleotide sequence that encodes a transgene and that further comprises nucleotide sequences necessary for packaging of the vector. Preferably, the retroviral transfer vector also comprises the necessary sequences for expressing the transgene in cells.

As used herein, "vector particle", "retroviral particle", "viral particle", "retroviral vector particle" refers to a replication-defective retrovirus carrying an RNA transcribed from a retroviral vector of the present invention. Preferably, the RNA comprises a transgene sequence (transgene RNA) transcribed from a retroviral transfer vector of the present invention.

As used herein, "packaging system" refers to a set of viral constructs comprising genes that encode viral proteins involved in packaging a recombinant virus. Typically, the constructs of the packaging system will ultimately be incorporated into a packaging cell.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871–875.

As used herein, a "third generation" lentiviral vector system refers to a lentiviral packaging system that has the characteristics of a second generation vector system, and that further lacks a functional tat gene, such as one from which the tat gene has been deleted or inactivated. Typically, the gene encoding rev is provided on a separate expression construct. See, e.g., Dull et al., 1998, J. Virol. 72(11):8463–8471.

As used herein, "pseudotyped" refers to the replacement of a native envelope protein with a heterologous or functionally modified envelope protein.

As used herein, "heterologous" refers to that which is not endogenous to, or naturally occurring in, a referenced sequence, molecule (including e.g., a protein), cell, tissue, or organism. For example, a heterologous sequence of the present invention can be derived from a different species, or from the same species but substantially modified from an original form. Also for example, a nucleic acid sequence that is not normally expressed in a cell is a heterologous nucleic acid sequence.

As used herein, a "functionally modified" protein refers to a protein that has a different or altered activity or property of the protein from which the functionally modified protein was derived. Preferably, a heterologous or functionally modified envelope protein of the present invention has a different cellular or binding specificity as compared to the envelope protein from which the heterologous or functionally modified protein was derived. A functionally modified envelope protein of the present invention can be generated by modifying (e.g., by point mutation, deletion, fusion, or chemical coupling) an envelope protein from which it is derived. For example, a functionally modified envelope protein of the present invention may be an envelope protein that has a mutation and/or deletion, as compared to the envelope protein from which it was derived. Also, for example, a functionally modified envelope protein of the present invention may be an envelope protein that is fused or coupled to a ligand that binds to a specific cellular target (e.g., a receptor) and, thereby, the cellular and/or binding specificity of the envelope protein is altered, as compared to the envelope protein from which it was derived.

As used herein, a "gp64" gene refers to a baculoviral gp64 envelope gene. The sequence of a gp64 gene can be derived from the baculoviridae family. Representative gp64 genes and methods for preparing them are described in Monsma and Blissard, 1995, J. Virol. 69(4):2583–95; Blissard and Rohrmann, 1989, Virology 170(2):537–55; and Blissard and Mons U.S. Pat. Nos. 5,750,383 and 5,750,383. The gp64 or other baculoviral envelope gene can be from the baculoviridae family. For example, the gp64 or other baculoviral envelope gene can be from *Autographa californica* nucleopolyhedrovirus (AcMNPV), *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, *Dhori virus, Thogoto virus, Antheraea pernyi* nucleopolyhedrovirus, or Batken virus. Preferably, the gp64 envelope gene is an AcMNPV gp64 envelope gene.

"Gene" as used herein refers to a nucleic acid sequence encoding at least one open reading frame that is capable of encoding a polypeptide or protein.

As used herein, "transgene" refers to a polynucleotide that can be expressed, via recombinant techniques, in a non-native environment or heterologous cell under appropriate conditions. The transgene may be derived from the same type of cell in which it is to be expressed, but introduced from an exogenous source, modified as compared to a corresponding native form and/or expressed from a non-native site, or it may be derived from a heterologous cell. "Transgene" is synonymous with "exogenous gene", "foreign gene" and "heterologous gene".

As used herein, a "therapeutic" gene refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

As used herein, "subject" refers to the recipient of the therapy to be practiced according to the invention. The subject can be any animal, including a vertebrate, but will preferably be a mammal. If a mammal, the subject will preferably be a human, but may also be a domestic livestock, laboratory subject or pet animal.

As used herein, "significant toxicity" refers to a level of toxicity that contraindicates clinical use as determined by an art-accepted measure of toxicity. Examples of art-accepted measures of toxicity include, but are not limited to, elevated serum levels of an enzyme or other substance associated with liver toxicity, such as sGPT, creatinine, alkaline phosphatase and alanine aminotransferase (ALT). In one embodiment, elevated serum levels means higher than the upper limit of the normal range.

As used herein, "cytoxicity" refers to a level of toxicity that results in cell death, arrest in cell growth, or inactivation of cellular functions important for the viability of a cell.

As used herein, a "therapeutically acceptable amount" of a substance refers to a sufficient quantity of the substance that an amelioration of adverse symptoms or protection against adverse symptoms can be detected in a subject treated with the substance.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, *Remington's Pharmaceutical Sciences,* 18th edition, A. Gennaro, ed., Mack Publishing Co., Easton, Pa., 1990).

Reference is made herein to techniques commonly known in the art. Guidance in the application of such techniques can be found, e.g., in Ausubel et al. eds., 1995, Current Protocols In Molecular Biology, and in Sambrook et a., 1989, Molecular Cloning: A Laboratory Manual, Cold Spring Harbor Laboratory Press, NY, the contents of which are incorporated herein by reference.

The patents and publications cited throughout the specification are incorporated herein by reference.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Packaging Systems

The present invention provides retroviral packaging systems for generating producer cells and producer cell lines that produce pseudotyped retroviruses, and methods of making such packaging systems. Accordingly, present invention also provides producer cells and cell lines generated by introducing a retroviral transfer vector into such packaging systems (e.g., by transfection or infection), and methods of making such packaging cells and cell lines.

The packaging systems of the present invention comprise at least two packaging vectors: a first packaging vector which comprises a first nucleotide sequence comprising a gag, a pol, or gag and pol genes; and a second packaging vector which comprises a second nucleotide sequence comprising a heterologous or functionally modified envelope gene. In a preferred embodiment, the heterologous envelope gene is a baculovirus envelope gene, e.g., a gp64 envelope gene. In another preferred embodiment, the retroviral elements are derived from a lentivirus, such as HIV. Preferably, the vectors lack a functional tat gene and/or functional accessory genes (vif, vpr, vpu, vpx, nef). In another preferred embodiment, the system further comprises a third packaging vector that comprises a nucleotide sequence comprising a rev gene. The packaging system can be provided in the form of a packaging cell that contains the first, second, and, optionally, third nucleotide sequences.

The invention is applicable to a variety of retroviral systems, and those skilled in the art will appreciate the common elements shared across differing groups of retroviruses. The description herein uses lentiviral systems as a representative example. However, all retroviruses share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by the env gene; CA (p24), MA (p17) and NC (p7–11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each, for gagpol, rev, envelope and the transfer vector. Regardless of the generation of packaging system employed, gag and pol can be provided on a single construct or on separate constructs.

The packaging vectors of the present invention comprise one or more genes encoding retroviral packaging elements, wherein each gene is operably linked to an expression control sequence. In one embodiment, the vector is a plasmid. In addition, other vectors suitable for use in the packaging systems of the present invention are known in the art and include, for example, viral vectors.

Typically, the packaging vectors are included in a packaging cell, and are introduced into the cell via transfection, transduction or infection. Methods for transfection, transduction or infection are well known by those of skill in the art. A retroviral transfer vector of the present invention can be introduced into a packaging cell line, via transfection, transduction or infection, to generate a producer cell or cell line. Accordingly, the present invention further provides producer cells and cell lines that comprise the packaging system of the invention and a retroviral transfer vector. The producer cells or cell lines of the present invention are capable of producing a recombinant retrovirus that is pseudotyped with a heterologous or functionally modified envelope protein (e.g., a baculovirus envelope protein) and carries a transgene. The producer cells and cell lines can be cultured in media and the pseudotyped retrovirus recovered from the culture media and titrated using standard methods. Further, the pseudotyped retrovirus of the present invention is capable of infecting a host cell and, thereby, delivering the transgene to the host cell such that the transgene is expressed in the host cell.

The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400–11406, which describe packaging cells. Further description of stable cell line production can be found in Dull et al., 1998, J. Virology 72(11):8463–8471; and in Zufferey et al., 1998, J. Virology 72(12):9873–9880

Zufferey et al., 1997, Nature Biotechnology 15:871–875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

The packaging vectors of interest may contain additional changes to the packaging functions to enhance lentiviral protein expression and to enhance safety. For example, all of the HIV sequences upstream of gag can be removed. Also, sequences downstream of envelope can be removed. Moreover, steps can be taken to modify the vector to enhance the splicing and translation of the RNA.

Optionally, a conditional packaging system is used, such as that described by Dull et al., 1998, J. Virology 72(11):8463–8471. Also preferred is the use of a self-inactivating vector (SIN), which improves the biosafety of the vector by deletion of the HIV-1 long terminal repeat (LTR) as described, for example, by Zufferey et al., 1998, J. Virology 72(12):9873–9880. Inducible vectors can also be used, such as through a tet-inducible LTR.

Retroviral Vectors and Retroviruses

The present invention further provides retroviral vectors for use in retroviral packaging systems to generate producer cells and cell lines that produce a high titer pseudotyped retrovirus capable of selectively infecting human and other mammalian cells. Accordingly, the present invention also provides such pseudotyped retroviruses and methods of producing such retroviruses. The retroviral vectors of the present invention, include e.g., retroviral transfer vectors comprising one or more transgene sequences and retroviral packaging vectors comprising one or more packaging elements. In particular, the present invention provides pseudotyped retroviral vectors encoding a heterologous or functionally modified envelope protein for producing pseudotyped retrovirus. Preferably, the envelope protein is a baculovirus envelope protein, e.g., gp64.

In preferred embodiments, the heterologous or functionally modified envelope protein of the present invention has a different cellular or binding specificity as compared to the envelope protein from which the heterologous or functionally modified protein was derived. Additionally, the envelope protein from which a heterologous or functionally modified envelope protein is derived can be a native envelope protein or non-native (or heterologous) envelope protein.

The replacement of a native envelope protein with a heterologous or functionally modified envelope protein can be performed using standard recombinant methods. As used herein, with reference to a protein, "replace" or "replacement" or grammatical equivalents thereof, refers to any alteration resulting in a different biological or physical property or activity of the protein. One skilled in the art would know how to "replace" a native envelope protein with a heterologous or functionally modified envelope protein, e.g., by mutation, deletion, or substitution of a nucleic acid or amino acid sequence encoding the protein from which the heterologous or functionally modified envelope protein is derived. Additionally, a functionally modified envelope protein can be made by fusion or chemical coupling of a ligand or protein to the envelope protein from which it was derived.

In preferred embodiments, the pseudotyped retroviral viral vectors of the present invention comprise a nucleic acid sequence encoding a native envelope protein that is replaced by a sequence encoding a heterologous or functionally modified envelope protein which has a different biological or physical property or activity as compared to the protein from which it was derived. For example, a heterologous or functionally modified envelope protein of the present invention can have a different cellular or binding specificity as compared to the envelope protein from which it was derived. In particular, the pseudotyped retroviral vectors of the present invention have enhanced efficiency through tissue-specific infectivity as well as reduced cytotoxicity and immunogenicity as compared to retroviral vectors pseudotyped with VSV-G. Also, for example, a heterologous or functionally modified envelope protein of the present invention can have increased titer, stability, or complement resistance as compared to the envelope protein from which it was derived.

The pseudotyped retroviral vectors of the present invention can be constructed by using known methods and sequences. In particular, methods of making retroviral vectors and retroviral sequences are known. Further, methods of making pseudotyped retroviral vectors encoding a heterologous envelope protein and envelope sequences are known.

The sequence of a heterologous or functionally modified envelope protein of the present invention can be derived from the sequence of an envelope protein of the baculoviridae family. Preferably, the sequence of the heterologous or functionally modified envelope protein of the present invention is derived from the baculoviral envelope protein gp64. Representative gp64 genes and methods of preparing them are known and described, e.g., in Monsma & Blissard, 1995, J. Virol. 69(4):2583–95; Blissard & Rohrmann, 1989, Virology 170(2):537–55; and Blissard & Monsma, U.S. Pat. Nos. 5,750,383 and 5,750,383. For example, a gp64 or other suitable baculovirus envelope genes can be derived from *Autographa californica* nucleopolyhedrovirus (AcMNPV), *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, *Dhori virus, Thogoto virus, Antheraea pernyi* nucleopolyhedrovirus or Batken virus. Preferably, the gp64 envelope gene is an AcMNPV gp64 envelope gene.

However, the heterologous or functionally modified envelope proteins of the present invention are not limited to baculovirus. For example, suitable heterologous or functionally modified envelope proteins can be derived from an envelope protein of a Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) or Rous sarcoma virus (RSV).

The core sequence of the retroviral vectors of the present invention may be readily derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods of the present invention includes, but is not limited to, lentivirus. Other retroviruses suitable for use in the compositions and methods of the present invention include, but are not limited to, Avian Leukosis Virus, Bovine Leukemia Virus, Murine Leukemia Virus, Mink-Cell Focus-inducing Virus, Murine Sarcoma Virus, Reticuloendotheliosis virus and Rous Sarcoma Virus. Particularly preferred Murine Leukemia Viruses include 4070A and 1504A (Hartley and Rowe, J. Virol. 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Other lentivirus include, a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768–1771, including Table 1, incorporated herein by reference).

As used herein, a first polynucleotide sequence is "derived from" a second polynucleotide sequence if it has the same or substantially the same base pair sequence as a region of the second polynucleotide sequence, its cDNA, complements thereof, or if it displays sequence identity as described above. Similarly, a first polypeptide sequence is "derived from" a second polypeptide sequence if it is (i) encoded by a first polynucleotide sequence derived from a second polynucleotide sequence, or (ii) displays sequence identity to the second polypeptide sequence as described above.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482–489 (1981). This algorithm can be extended to use with peptide sequences using the scoring matrix developed by Dayhoff, Atlas of Protein Sequences and Structure, M. O. Dayhoff ed., 5 suppl. 3:353–358, National Biomedical Research Foundation, Washington, D.C., USA, and normalized by Gribskov, Nucl. Acids Res. 14(6):6745–6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. Details of these programs can be found at the following internet address: NCBI website.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10–12 nucleotides and up to 5000 nucleotides, and even more preferably 15–20 nucleotides, up to the number of nucleotides present in the full-length sequences described herein (e.g., see the Sequence Listing and claims), including all integer values falling within the above-described ranges.

In preferred embodiments, a retroviral vector sequence of the present invention encoding a packaging element, transfer gene or heterologous or functionally modified envelope protein is operably linked with at least one regulatory sequence, e.g., a promoter and/or enhancer. The regulatory sequence can be any eukaryotic promoter and/or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

Preferably, the regulatory sequence is one which is not endogenous to the lentivirus from which the retroviral vector sequence is derived. For example, if the vector sequence is derived from a lentivirus, the lentiviral regulatory sequence found in the lentivirus LTR can be replaced by a regulatory element which does not originate from the lentivirus.

Preferably, the retroviral vector sequences employed in the retroviral packaging vectors and transfer vectors of the present invention include at least one locus defining element (s), or other elements which control gene expression by other means such as alternate splicing, nuclear RNA export, post-translational modification of messenger, or post-transcriptional modification of protein. Such vector sequences also preferably include a packaging signal, long terminal repeats (LTRs) or portion thereof, and positive and negative strand primer binding sites appropriate to the retrovirus used (if these are not already present in the retroviral vector sequence). Optionally, a retroviral vector sequence of the present invention may include a signal which directs polyadenylation, selectable markers such as Neomycin resistance, TK, hygromycin resistance, phleomycin resistance, histidinol resistance, or DHFR, as well as one or more restriction sites and a translation termination sequence. In some embodiments, the retroviral vector sequences of the present invention include a 5' LTR, a tRNA binding site, a packaging signal, an origin of second strand DNA synthesis, and a 3' LTR or a portion thereof.

Suitable tRNA binding sites and origins of second strand DNA synthesis are known and may be readily identified by one of skill in the art. For example, a retroviral tRNA can bind to a tRNA binding site by Watson-Crick base pairing, and can be carried with the retrovirus genome into a viral particle and utilized as a primer for DNA synthesis by reverse transcriptase. Consequently, a tRNA binding site may be readily identified based on its location just downstream from a 5' LTR. The origin of second strand DNA synthesis is also referred to as the polypurine tract, is located just upstream of the 3' LTR.

In one embodiment, the retroviral vectors of the present invention are self-inactivating (SIN) retroviral vectors. SIN retroviral vectors and methods of making such vectors are known in the are (see e.g., Zufferey et al. (1998) 72:9873–9880; Dull et al. (1998) J. Virol. 72:8463–8471; Xu et al. (2001) Molecular Therapy 3:1–8). Generally, a SIN retroviral vector can be constructed by introducing a deletion or mutation in a retroviral transcriptional regulatory sequence of a retroviral vector to generate a SIN retroviral vector which is replication incompetent and incapable of transcribing a full-length vector RNA in mammalian cells transduced with such vectors.

In a preferred embodiment of the present invention, the retroviral vector of the present invention has a 3'LTR which contains a deletion or mutation that inactivates the transcriptional activity of that 3'LTR ("SIN3'LTR"), thereby, making the vector a SIN retroviral vector. In this embodiment, during the retroviral processing and reverse transcription of the full-length vector RNA, the sequences of the 5'LTR are replaced with the sequences of the SIN3'LTR.

Transcription of a full-length vector RNA can be driven by a promoter in the 5'LTR of a retroviral vector sequence of the present invention. However, the location of the promoter is not limited to the 5'LTR and can be placed in any location where the promoter is operably linked to the respective vector sequence. As used herein "operably linked" refers to an arrangement of elements wherein the components so described are configured so as to perform their usual or intended function. For example, a given promoter operably linked to a gene sequence, or other sequence encoding a protein, is capable of effecting the expression of that sequence. However, the promoter need not be contiguous with the coding sequence, so long as it functions to direct the expression of the operably linked sequence.

The 5' LTR of a retroviral vector sequence of the present invention can be modified by substituting part or all of the transcriptional regulatory elements of the U3 region with heterologous enhancer/promoters. Such changes can be made to enhance the expression of retroviral vector RNA in producer cells and producer cell lines; to allow retroviral vector production in the absence of a HIV tat gene; and to remove an upstream wild-type copy of an HIV LTR that can recombine with the 3' deleted version to "rescue" a SIN retroviral vector. Thus, in some embodiments, the SIN retroviral vector sequences of the present invention have such alterations at the 5' LTR and can be used, e.g., in combination with packaging cells that do not express tat. to generate producer cells or cell lines.

For example, transcription from the HIV LTR is dependent on the transactivator function of the tat protein. In the presence of tat, which can be expressed by a packaging vector, transcription of retroviral vector RNA from the HIV LTR can be strongly stimulated. Where the retroviral vector RNA has a full complement of packaging signals, the RNA is efficiently encapsidated into infectious virions and can be efficiently transferred to target cells. The amount of retroviral vector RNA available for packaging by cells can be a rate-limiting step in the production of recombinant retrovirus carrying a retroviral vector RNA.

The enhancer or the enhancer and promoter regions of a 5' LTR can be substituted, e.g., with the enhancer or the enhancer and promoter of a human cytomegalovirus (CMV) or a murine Rous sarcoma virus (RSV), respectively. The enhancer or the enhancer and promoter regions of a 5' LTR can also be substituted, e.g., with a regulatable promoter such as the tetracycline-inducible promoter.

In a preferred embodiment, a retroviral vector of the present invention has significantly improved biosafety as compared to known retroviral vectors because it has no wild-type copy of the HIV LTR either at the 5' or at the 3' end, and is used in conjunction with tat-less packaging vectors as described herein. Thus, in some preferred embodiments, the present invention provides for packaging vectors wherein the tat sequences are functionally deleted (i.e., the activity and/or function of tat is inactivated). For example, the tat gene can be deleted, in part or in whole, or various point mutations or other mutations can be made to the tat sequence to inactivate the gene.

Where a retroviral vector of the present invention encodes a cytotoxic gene (i.e., a gene that expresses a product deleterious to a host cell), an inducible promoter system is preferably operably linked to the transcription unit of the cytotoxic gene such that the expression of that gene can be regulated to minimize host toxicity when gene expression is not required.

For example, the tetracycline-regulatable gene expression system of Gossen & Bujard (Proc. Natl. Acad. Sci. (1992) 89:5547–5551) can be employed to provide for inducible expression of a gene when tetracycline is withdrawn from the transferred cell. Thus, in one preferred embodiment, the tet/VP16 transactivator is present on a first vector and a coding sequence for a cytotoxic gene is cloned downstream from a promoter controlled by tet operator sequences on another vector.

In addition, a retroviral vector of the present invention can comprise an antigen-binding portion of an antibody or a recombinant antibody-type molecule, such as a single chain antibody, to direct the retroviral vector to a specific cellular target. Those of skill in the art would know of, or could readily ascertain without undue experimentation, specific methods to achieve delivery of a retroviral vector to a specific cellular target.

The present invention also provides methods of producing a pseudotyped retrovirus. In preferred embodiments, the methods comprise transforming a host cell with a first nucleotide sequence comprising a gag, a pol, or gag and pol genes; and a second nucleotide sequence comprising a heterologous or functionally modified envelope protein. Preferably, the envelope protein is a baculoviral envelope protein, e.g., gp64. In another preferred embodiment, the retroviral elements are derived from a lentivirus, e.g., HIV. Preferably, the vectors lack a functional tat gene and/or functional accessory genes (vif, vpr, vpu, vpx, nef). In another preferred embodiment, the methods further comprise transforming the host cell with a third nucleotide sequence that comprises a rev gene. Optionally, the method further comprises transforming the host cell with a transfer vector sequence encoding a transgene operably linked to an expression control sequence. The host cell can be cultured under conditions suitable for viral production, and retrovirus carrying transfer vector RNA encoding the transgene can be recovered from the culture medium.

The techniques used to construct vectors, and to transfect and to infect cells, are practiced widely in the art. Practitioners are familiar with the standard resource materials which describe specific conditions and procedures. Construction of the vectors of the present invention employs standard ligation and restriction techniques which are well understood in the art (see Maniatis et al., in Molecular Cloning: A Laboratory Manual, Cold Spring Harbor Laboratory, N.Y., 1982). Isolated plasmids, DNA sequences or synthesized oligonucleotides are cleaved, tailored and religated in the form desired.

Conventional methods can be used to propagate the viruses used in the invention (see, e.g., Burleson, et al., 1992, Virology: A Laboratory Manual, Academic Press, Inc., San Diego, Calif.; and Mahy, ed., 1985, Virology: A Practical Approach, IRL Press, Oxford, UK). Conventional conditions for propagating viruses are suitable for allowing expression of a baculoviral envelope protein on the surface of a retrovirus particle used in the invention.

Methods for the large-scale production of safe and efficient retrovirus packaging lines for use in immunotherapy protocols is described in Farson et al., 1999, J. Gene Medicine 1:195–209. Additional guidance on the production and use of lentiviral vectors is provided in U.S. Pat. No. 6,165,782, issued Dec. 26, 2000, and in PCT Application No. US 00/11097, published Nov. 29, 2000. Transduction efficiency can be enhanced and toxicity minimized or eliminated through the selection of elements for the vector construct as well as through vector purification or concentration. Such methods of purification and of concentration are well known in the art.

Preferred is the use of pseudotyped lentiviral vectors of the present invention that are capable of high infectivity (e.g., more than 20% of target cells expressing transgene, preferably more than 25% of target cells expressing, or an infectivity of at least about $5 \times 10^7$ TU/µg p24 Gag antigen) of quiescent as well as proliferating cells. Also preferred is the use of a purification protocol sufficient to produce a viral stock that is substantially free of non-infectious contaminants. In a preferred embodiment, the pseudotyped lentivirus of the present invention are centrifuged at low speed, filtered, and then concentrated by high speed centrifugation, such as at about 19,500 rpm.

In one embodiment, the pseudotyped retrovirus of the present invention has a titer of $5 \times 10^4$ infectious units/ml. Preferably, pseudotyped retrovirus of the present invention has at least a titer of $1 \times 10^5$, or more preferably, at least $5 \times 10^5$ infectious units/ml, and most preferably, at least $5 \times 10^6$ infectious units/ml. The titer can be determined by known or conventional infectivity assay on a variety of cells, e.g., 293T, HeLa or HUH7 hepatoma cells.

Retroviral-Mediated Gene Transfer

The present invention additionally provides methods for delivering a transgene to a cell, in vivo, in vitro or ex vivo using the pseudotyped retrovirus of the present invention. Also provided are methods of treating a subject and of delivering a therapeutic transgene to cells of a subject using the pseudotyped retrovirus of the present invention. In some embodiments, the transgene is delivered to dividing or quiescent cells in a subject, such as liver cells. The method comprises using the retroviral transfer vectors of the present invention to transduce a cell with a sequence encoding a transgene. Preferably, the transgene is a therapeutic transgene. In preferred embodiments, significant toxicity is not caused in the subject. Toxicity can be minimized or eliminated by use of a vector of the invention, such as those described herein and having an infectivity of at least about $5 \times 10^7$ TU/µg p24$^{Gag}$ antigen.

The pseudotyped retroviral particles of the invention can be administered to a subject parenterally, preferably intravascularly (including intravenously). When administered parenterally, it is preferred that the pseudotyped vector particles of the present invention be given in a pharmaceutical vehicle suitable for injection such as a sterile aqueous solution or dispersion. Following administration, the subject is monitored to detect changes in gene expression. Dose and duration of treatment is determined individually depending on the condition or disease to be treated. A wide variety of conditions or diseases can be treated based on the gene expression produced by administration of the gene of interest in the vector of the present invention.

The dosage of retroviral vector delivered using the methods of the invention will vary depending on the desired response by the host and the vector used. Generally, it is expected that up to 100–200 µg of DNA or RNA can be administered in a single dosage, although a range of 0.5 mg/kg body weight to 50 mg/kg body weight will be suitable for most applications.

Pseudotyping can extend the tissue tropism of the retroviral vectors of the present invention and can increase efficiency of gene transfer into cells. Accordingly, the present invention additionally provides methods of delivering a transgene to a cell using pseudotyped retroviral vectors.

In preferred embodiments, the transgene is a therapeutic transgene. However, the compositions and methods of the present invention can be used to produce any non-retroviral vector sequence, or expression products thereof, in cells specifically for the purpose of reproduction of that sequence (e.g., for cloning) or expression product (e.g., for therapeutic or commercial use). Thus, in one embodiment, the recombinant retrovirus of the present invention act as a cloning vehicle and has utility as such for the reproduction of any transgene sequence that can be packaged into recombinant retrovirus of the present invention for infection and transduction of a cell such that the cell expresses the transgene sequence. In preferred embodiments, the recombinant retrovirus of the present invention can be used for treatment of diseases in a subject where there is defective or deficient expression of gene products, a viral infection, tumor, or cancer.

"Gene transfer" or "gene delivery" as used herein refers to the introduction or delivery of a nucleic acid sequence (e.g., a DNA or RNA sequence) of interest into a host cell (e.g., a target cell, packaging cell, or producer cell) resulting in: 1) the transient expression of non-integrated transferred DNA; 2) extrachromosomal replication and expression of transferred replicons (e.g., episomes); or 3) integration of transferred genetic material into the genomic DNA of host cells.

Retroviral-mediated gene transfer, based upon ex vivo transduction of target cells, is known and, e.g., has been employed in humans. The ability to target delivery and expression of selected genes or nucleic acid sequences into desirable tissue cells in an in vivo setting using retroviral vectors is also known. Thus, retroviral-mediated gene transfer using the compositions of the present invention can be used to effectively treat genetic disorders, tumors and viral infections in a subject. Genetic disorders include, e.g., diseases resulting from lesions in genes. Such diseases may include, for example, hematopoietic and bone marrow disorders, metabolic disorders resulting from defects in liver enzymes and diseases of the central nervous system. Potential clinical applications are thus numerous for such retroviral-mediated gene transfer using the compositions of the present invention.

For some diseases, introduction of a functional homolog of the defective gene and production of even small amounts of the gene product could have a beneficial effect. Other diseases may require a specific amount of gene product to be produced at a specific time, typically in response to a physiological signal (regulated gene expression). An example of such diseases is diabetes, where insulin production requires such regulated gene expression. In such cases gene replacement, rather than gene augmentation which is currently in practice, would be indicated. Otherwise attempts can be made to correct the underlying genetic defect by using genes along with their native regulatory switches (gene augmentation). In other cases, where it is not necessary to correct the genetic lesion in the cell type that exhibits the defect, the gene may be introduced into a different cell type. This is usually true for genes either encoding secretory proteins or enzymes which catalyze the production of secretory products. An example is the case of Parkinson disease where retrovirally transduced fibroblasts encoding tyrosine hydroxylase and capable of making dopamine were intracerebrally implanted in rats. See Wolff, Proc. Natl. Acad. Sci. USA 86:9011–15(1989). However, most genetic diseases require that the defective gene be replaced in the relevant cell type.

Because malignancies appear to result from a number of genetic lesions, both inherited and acquired, which appear to activate oncogenes and/or inactivate tumor suppressor genes, gene therapy applications to treat tumors can take several approaches. One strategy is to enhance the cytotoxic effects of the body's natural defense mechanisms against tumor cells, for example using tumor infiltrating lymphocytes by expressing certain gene products (see e.g., Kasid, Proc. Nat. Acad. Sci. USA 87:473–77(1990); Rosenberg, Cancer Res. Supp. 51:50745–50795(1991); Rosenberg, J. Am. Med. Assn. 268:2614–19(1992); Anderson, Science 256:808–13(1992)). A second approach is directed toward inhibiting the activity of dominantly acting oncogenes (see e.g., Tubiana, Eur. J. Cancer 27:936–39(1991)). Another strategy involves targeted delivery into tumor cells of the genes encoding toxic products or genes conferring sensitivity to toxic drugs, e.g., the thymidine kinase gene of the herpes simplex virus (HSV-TK) (see e.g., Moolten and Wells, J. Natl. Cancer Inst. 82:297–300(1990) and Culver, Science 256:1550–52(1992)). Retroviral vectors transducing HSV-tk gene into tumor cells can enhance the incorporation of nucleoside analogs such as acyclovir and ganciclovir and thereby exhibit tumoricidal effect upon administration of these drugs.

Gene therapy also finds utility in the treatment of virally induced conditions, such as HIV and HTLV-I infections. The regulatory proteins or response elements of HIV and HTLV-I necessary for virus production are potential targets. Mutants of these proteins could be introduced to compete with the native viral proteins. In addition, antisense RNAs complementary to retroviral RNAs are being employed to specifically inhibit replication of HIV and HTLV-I (see e.g., Rhodes and James, AIDS 5:145–51(1991); von Rueden and Gilboa, J. Virol. 63:677–82(1989)). Retroviral vectors carrying HIV-specific antisense sequences or ribozymes could be used to inhibit expression of HIV for cellular immunization. Triple stranded RNA complexes, in which double-stranded RNA is locked into conformation by a third strand could prove an effective way of silencing viral gene expression by designing retroviral vectors encoding an antisense and an anti parallel triple stranded RNA on a single molecule from a retroviral vector (see, e.g., Giovannangeli, J. Am. Chem. Soc. 113:7775–77(1991).

In general, retroviral vectors offer advantages over other viral gene transfer vehicles and other gene transfer methods including, for mammalian systems, electroporation, $CaPO_4$ precipitation, DEAE-dextran, direct DNA injection and lipofection. Retroviruses carry genetic information in the RNA form, reverse transcribing a DNA form upon infection that efficiently integrates into the genomic DNA of the infected cell and, thereby, offer stable propagation of the integrated sequence in the progeny cells of the transduced parent cell. Retroviral integration is site-specific with respect to viral ends, and the provirus is usually intact and colinear with the viral genome, i.e., the LTR-gag-pol-env-LTR gene order is maintained by the provirus which, consequently, reduces the possibility of DNA rearrangements and/or deletions, as is commonly observed with random pathway integration. Cells infected with replication defective retroviral vectors do not express viral proteins and thus are not susceptible to immune clearance. In addition, the efficiency of gene transfer and stable expression in transduced cells can be very high with such vectors. For these reasons such retroviral vectors have been approved for use in human gene therapy.

While ex vivo therapeutic regimens have found success in treating certain genetic disorders, other disorders need to be treated using an in vivo therapeutic approach because the genetic disorder affect cell types not easily isolated. Thus, preferably, the packaged retroviral vector is not inactivated by specific host humoral or cellular immune responses or by non-specific responses such as complement or other blood factors. In such applications, it is also preferable that the retroviral vector infects only the cells in which the defect manifests itself. In a preferred embodiment, the expression of the therapeutic gene is controlled by regulatory elements that target expression to the relevant cell type.

Retroviruses can be classified according to their host range. For example, ecotropic murine retroviruses such as MuLV (MuLV-E) infect only murine cells. Xenotropic murine retroviruses such as MuLVs (MuLV-X) infect non-murine cells. Amphotropic murine retroviruses such as MuLVs (MuLV-A) infect both murine and non-murine cells, including human cells. As described herein, the host range and cell tropism is determined primarily by the viral envelope protein and the availability of specific receptor proteins on the host cells. Thus, using the compositions and methods of the present invention, the host range of a retrovirus can be altered by pseudotyping.

Other approaches to modifying the tissue-infecting capacity of retroviral vectors to achieve viral targeting involve the use of bivalent, streptavidin-linked antibodies. Other approaches involve generating functionally modified envelope proteins by fusion or chemical coupling of ligands or proteins that bind to specific cellular targets to an envelope protein. For example, one approach involves the fusion or chemical coupling of a ligand (e.g., a receptor or antibody) to an envelope protein. For example, by coupling the envelope protein to lactose, the protein becomes an artificial asialoglycoprotein which is internalized by specific receptors on hepatocyte cells (see e.g., Neda, J. Biol. Chem. 226:14143–46(1991)). An additional approach involves mutation of the receptor recognition region of the envelope gene to generate chimeric envelope proteins. For example, an engineered MoMuLV-E vector bearing a chimeric erythropoietin-envelope (EPO-envelope) protein on its surface has exhibited infectivity for cells that bear the EPO receptor, both of murine and human origin (see e.g., Kasahara, Science 266:1373–76(1994)). This chimeric construct has an EPO encoding sequence substituted for the N-terminal region of the envelope gene, and, although the chimeric MoMuLV-E construct exhibits tissue targeting, it requires complementation from the wild type envelope protein.

Transgene Sequences

The retroviral transfer vector sequences of the present invention can encode one or more transgene sequences (i.e., a gene or gene fragment, or more than one gene or gene fragment or other sequence encoding a protein). Any of the polynucleotide sequences described herein may be used to identify fragments or full-length coding sequences of the genes to which they are associated and may be suitable for use in the compositions and methods of the present invention. Methods of isolating fragments or full-length sequences of genes are well known in the art.

Such genes and/or gene fragments can comprise any sequence useful in gene therapy or for any other purpose (e.g., cloning or product production). See e.g. WO96/21014 and WO91/02805 for a description of nucleic acid sequences of therapeutic interest that can be introduced into the retroviral vectors of the invention. Preferably, the transgene sequence encodes a protein, e.g., a hormone, enzyme, receptor, or single chain antibody useful in gene therapy.

The transgene sequence can be any nucleic acid sequence of interest which can be transcribed. Generally, the transgene sequence encodes a polypeptide. Preferably, the polypeptide has some therapeutic benefit. For example, the polypeptide may supplement deficient or nonexistent expression of an endogenous protein in a host cell. The polypeptide can confer new properties on the host cell, such as a chimeric signaling receptor, see e.g., U.S. Pat. No. 5,359,046. The artisan can determine the appropriateness of a transgene sequence practicing techniques taught herein and known in the art. For example, the artisan would know whether a transgene sequence is of a suitable size for encapsidation and whether the transgene sequence product is expressed properly.

Preferably, a transgene sequence encoded by a retroviral vector sequence of the present invention is operably linked to a promoter that is internal to the transcription regulatory sequences of the retroviral vector sequence. "Operably linked" as used herein with reference to a transgene sequence refers to a functional linkage between a regulatory sequence and a transgene nucleic acid sequence resulting in expression of the transgene sequence in cells.

It may be desirable to modulate the expression of a gene regulating molecule in a cell by the introduction of a molecule using the compositions and methods of the invention. The term "modulate" envisions the suppression of expression of a gene when it is over-expressed or augmentation of expression when it is under-expressed. Where a cell proliferative disorder is associated with the expression of a gene, nucleic acid sequences that interfere with the expression of a gene at the translational level can be used. The approach can utilize, for example, antisense nucleic acid, ribozymes or triplex agents to block transcription or translation of a specific mRNA, either by masking that RNA with an antisense nucleic acid or triplex agent, or by cleaving same with a ribozyme.

Antisense nucleic acids are DNA or RNA molecules which are complementary to at least a portion of a specific mRNA molecule (Weintraub, Sci. Am. (1990) 262:40). In the cell, the antisense nucleic acids hybridize to the corresponding mRNA forming a double-stranded molecule. The antisense nucleic acids interfere with the translation of the mRNA since the cell will not translate a mRNA that is double-stranded. Antisense oligomers of about 15 nucleotides or more are preferred since such are synthesized easily and are less likely to cause problems than larger molecules when introduced into the target cell. The use of antisense methods to inhibit the in vitro translation of genes is well known in the art (see e.g., Marcus-Sakura, Anal. Biochem. (1988) 172:289).

Useful antisense nucleic acids also include small-interfering RNA (siRNA) molecules. Methods of using siRNA to inhibit gene expression are well known in the art (see e.g., U.S. Pat. No. 6,506,559).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinson's and other diseases. Antisense nucleic acids are also useful for the inhibition of expression of proteins associated with toxicity.

Use of an oligonucleotide to stall transcription can be by the mechanism known as the triplex strategy since the oligomer winds around double-helical DNA, forming a three-strand helix. Therefore, the triplex compounds can be designed to recognize a unique site on a chosen gene (see e.g., Maher et al., Antisense Res. and Dev. (1991)1(3):227; Helene, Anticancer Drug Dis. (1991) 6(6):569).

Ribozymes are RNA molecules possessing the ability to specifically cleave other single-stranded RNA in a manner analogous to DNA restriction endonucleases. Through the modification of nucleotide sequences which encode those RNA's, it is possible to engineer molecules that recognize and cleave specific nucleotide sequences in an RNA molecule (see e.g., Cech, J. Amer. Med Assn. (1988) 260:3030). A major advantage of that approach is only mRNA's with particular sequences are inactivated.

The desired transgene sequence or sequences are preferably non-retroviral sequences that are inserted into a retroviral transfer vector sequence of the present invention. However, in some cases a desired therapeutic gene may be a retroviral gene, e.g., a sequence encoding an HIV structural protein capable of inducing an anti-HIV immune response. Such therapeutic retroviral sequences are preferably recombinant or heterologous with respect to the retroviral vector sequence (e.g., an HIV-1 therapeutic gene sequence is inserted into a MuLV vector sequence of the present invention).

For example, to enhance the body's natural cytotoxic defense mechanisms, recombinant retroviral vectors of the invention may include sequences which stimulate the production of, or genetically modify, tumor infiltrating lymphocytes (TIL). TIL transduced ex vivo with a retroviral vector expressing neo gene have been employed to study their homing sites in the human hosts. Similarly, TIL transduced with tumor necrosis factor (TNF) have been used to treat human subjects with advanced melanoma. In addition, TIL transduced with chimeric T cell receptor (TcR) consisting of the constant region of the TcR and the variable region of a monoclonal antibody can be redirected to lyse cancer cells recognized by the monoclonal antibody.

The nucleic acid sequence inserted into the retroviral vector can be, e.g., a viral structural gene that is capable of inducing an immune response against a viral infection in a subject. Additionally, the nucleic acid sequence inserted into the retroviral vector can be, e.g., any other gene useful for vaccination or immunization of a subject (e.g., a bacteria or protozoa, particularly a pathogen, or a gene encoding a tumor antigen). In the particular case of disease caused by HIV infection, where immunostimulation is desired, the antigen generated from a recombinant retrovirus may be in a form which will elicit either or both an HLA class I- or class II-restricted immune response. In the case of HIV envelope antigen, for example, the antigen is preferably selected from gp 160, gp 120, and gp 41, which have been modified to reduce their pathogenicity. In particular, the selected antigen is modified to reduce the possibility of syncytia, to avoid expression of epitopes leading to a disease enhancing immune response, to remove immunodominant, but haplotype-specific epitopes or to present several haplotype-specific epitopes, and allow a response capable of eliminating cells infected with most or all strains of HIV.

The haplotype-specific epitopes can be further selected to promote the stimulation of an immune response within an animal which is cross-reactive against other strains of HIV. Antigens from other HIV genes or combinations of genes, such as gag, pol, rev, vif, nef, prot, gag/pol, gag prot, etc., may also provide protection in particular cases. HIV is only one example. This approach should be effective against many virally linked diseases or cancers where a characteristic antigen (which does not need to be a membrane protein) is expressed, such as in HPV and cervical carcinoma, HTLV-I-induced leukemias, prostate-specific antigen (PSA) and prostate cancer, mutated p53 and colon carcinoma and melanoma, melanoma specific antigens (MAGEs), and melanoma, mucin and breast cancer.

A variety of cytokine or immunomodulatory genes may be inserted into the retroviral vectors of the invention. Representative examples of immunomodulatory factors include cytokines, such as IL-1, IL-2 (see e.g., Karupiah et al., J. Immunology 144:290–298, 1990; Weber et al., J. Exp. Med. 166:1716–1733,1987; Gansbacher et a., J. Exp. Med. 172:1217–1224, 1990; U.S. Pat. No. 4,738,927), IL-3, IL-4 (see e.g., Tepper et al., Cell 57:503–512, 1989; Golumbek et al., Science 254:713–716, 1991; U.S. Pat. No. 5,017,691), IL-5, IL-6 (see e.g., Brakenhof et al., J. Immunol. 139:4116–4121, 1987; WO 90/06370), IL-7 (see e.g., U.S. Pat. No. 4,965,195), IL-8, IL-9, IL-10, IL-11, IL-12, IL-13 (see e.g., Cytokine Bulletin, Summer 1994), IL-14 and IL-15, particularly IL-2, IL-4, IL-6, IL-12, and IL-13, alpha interferon (see e.g., Finter et al., Drugs 42(5):749–765, 1991; U.S. Pat. No. 4,892,743; U.S. Pat. No. 4,966,843; WO 85/02862; Nagata et al., Nature 284:316–320, 1980; Familletti et al., Methods in Enz. 78:387–394,1981; Twu et al., Proc. Natl. Acad. Sci. USA 86:2046–2050,1989; Faktor et a., Oncogene 5:867–872, 1990), beta interferon (see e.g., Seif et al., J. Virol. 65:664–671, 1991), gamma interferons (see e.g., Radford et al., The American Society of Hepatology 2008–2015, 1991; Watanabe et al., PNAS 86:9456–9460, 1989; Gansbacher et a., Cancer Research 50:7820–7825, 1990; Maio et al., Can. Immunol. Immunother. 30:34–42, 1989; U.S. Pat. No. 4,762,791; U.S. Pat. No. 4,727,138), G-CSF (see e.g., U.S. Pat. Nos. 4,999,291 and 4,810,643), GM-CSF (WO 85/04188), tumor necrosis factors (TNFs) (see e.g., Jayaraman et al., J. Immunology 144:942–951, 1990), CD3 (see e.g., Krissanen et al., Immunogenetics 26:258–266, 1987), ICAM-1 (see e.g., Altman et a., Nature 338:512–514, 1989; Simmons et al., Nature 331:624–627, 1988), ICAM-2, LFA-1, LFA-3 (see e.g., Wallner et al., J. Exp. Med. 166(4):923–932, 1987), MHC class I molecules, MHC class II molecules, B7 0.1–0.3, b.sub.2 -microglobulin (see e.g., Parnes et al., PNAS 78:2253–2257, 1981), chaperones such as calnexin, MHC linked transporter proteins or analogs thereof (see e.g., Powis et al., Nature 354:528–531,1991). Immunomodulatory factors may also be agonists, antagonists, or ligands for these molecules. For example soluble forms of receptors can often behave as antagonists for these types of factors, as can mutated forms of the factors themselves.

Within one embodiment, the gene encodes gamma-interferon. Immunomodulatory factors may also be agonists, antagonists, or ligands for these molecules. For example soluble forms of receptors can often behave as antagonists for these types of factors, as can mutated forms of the factors themselves. Genes encoding any of the cytokine and immunomodulatory proteins described herein can be expressed in a retroviral vector to achieve long term in vivo expression. Other forms of these cytokines which are know to those of skill in the art can also be used. For instance, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. As an additional example, nucleic acid sequences encoding the short and long forms of mCSF can be obtained as described in U.S. Pat. Nos. 4,847,201 and 4,879,227, respectively. Retroviral vectors expressing cytokine or immunomodulatory genes can be produced as described herein and in PCT publication number U.S. Ser. No. 94/02951 entitled "Compositions and Methods for Cancer Immunotherapy".

A variety of different forms of IGF-1 and IGF-2 growth factor polypeptides are also well known the art and can be incorporated into retroviral vectors for long term expression in vivo. See e.g. European Pat. No. 0123228B1, grant published on Sep. 19, 1993, entitled "Hybrid DNA Synthesis of Mature Insulin-like Growth Factors". As an additional example, the long term in vivo expression of different forms of fibroblast growth factor can also be effected by the methods of invention. See, e.g. U.S. Pat. No. 5,464,774, issued Nov. 7, 1995, U.S. Pat. No. 5,155,214, and U.S. Pat. No. 4,994,559, for a description of different fibroblast growth factors.

As additional examples, Factor VIII or Factor IX is useful for treatment of blood clotting disorders, such as hemophilia. Different forms of Factor VIII, such as the B domain deleted Factor VIII construct described in WO 96/21014 can be used to produce retroviral vectors expressing Factor VIII for use in the methods of the invention. In addition to clotting factors, there are a number of proteins which can be expressed in the retroviral vectors of the invention and which are useful for treatment of hereditary diseases. These include lactase for treatment of hereditary lactose intolerance, AD for treatment of ADA deficiency, and alpha-1 antitypsin for treatment of alpha-1 antitrypsin deficiency (see e.g., F. D. Ledley, J. Pediatics, 110,157–174 (1987); I. Verma, Scientific American (November, 1987) pp. 68–84; and PCT Publication WO 9527512 entitled "Gene Therapy Treatment for a Variety of Diseases and Disorders" for a description of gene therapy treatment of genetic diseases).

Alternatively, the recombinant retroviral vectors of the invention may include inducible genes encoding toxic products or genes which confer sensitivity to a toxic drug (suicidal vector approach). An example of a gene encoding a toxic product is the diphtheria toxin gene. An example of a gene that confers sensitivity to a toxic drug is the herpes simplex virus TK gene, which enhances the capacity of cells to metabolize and incorporate nucleoside analogs such as acyclovir and ganciclovir. A variety of other prodrug converting enzymes can also be used in the retroviral vectors of the invention (see, e.g., WO 95/14091 and EP 0 415 731 for a description of viral thymidine kinase and other prodrug converting systems for use in the retroviral vectors of the invention).

The recombinant retroviral vectors of the invention may include sequences, genes and/or gene fragments that encode either wild type or mutant forms of HIV or HTLV-I regulatory proteins or response elements that are required for virus production (e.g., gag and rev proteins and TAR sequence of HIV). These sequences may be modified by the addition, substitution, or deletion of nucleotides to change the reading frame of the protein or by N- or C-terminal truncation or deletion of an internal sequence of nucleotides to result in the expression of a trans dominant or competing defective HIV or HTLV-I protein or response element. Delivery of the recombinant retroviral vectors of the invention carrying these wild type, defective or trans dominant-acting mutant sequences would "arm" the transduced cells with "decoy" proteins to either directly inhibit the replication of the infecting virus or to cause replication incompetency and abortive infection by the packaged virion particles.

Alternatively, the recombinant retroviral vectors of the invention may include sequences coding for antisense RNA or ribozyme against HIV or HTLV-I that specifically inhibit virus replication and would therefore find use in therapeutic and probably the prophylactic treatments for HIV or HTLV-I infection.

The retroviral transfer vectors of the present invention may include sequences, genes and/or gene fragments to treat genetic diseases resulting from the expression of defective gene product/s such as severe combined immunodeficiency, chronic granulomatosis, Gaucher disease, sickle cell anemia, α- and β-thalasemias, Lesch-Nyhan syndrome, duchenne muscular distrophy, parkinson disease, emphysema, cystic fibrosis, phenylketonuria, familial hypercholesterolemia or hemophilia A and B. Such diseases are characterized by a deficiency of a specific gene product which affects a specific cell type.

For example, chronic granulomatosis is characterized by a deficiency in the cytochrome b which affects neutrophils; duchenne muscular dystrophy is characterized by a deficiency in the dystrophin which affects muscle cells; familial hypercholesterolemia is characterized by a deficiency in low-density lipoprotein which affects hepatocytes; gaucher disease is characterized by a deficiency in glucocerebrosidase which affects macrophages; hemophilia A and B is characterized by a deficiency in Factors VIII and IX which affects endothelial cells; lesch-nyhan hypoxanthine syndrome is characterized by a deficiency in phosphoribosyl transferase which affects basal ganglia; parkinson disease is characterized by a deficiency in dopamine which affects substantia nigra; phenylketonuria is characterized by a deficiency in phenylalamine hydroxylase which affects hepatocytes; severe combined immunodeficiency is characterized adenosine deaminase which affects T and B lymphocytes; sickle cell anemia is characterized by a deficiency in β-globin which affects erythrocytes; and α- and β-thalassemias are characterized by a deficiency in α- and β-globin which affects erythrocytes.

Within the recombinant retroviral vectors of the invention, the desired sequences, genes and/or gene fragments can be inserted at several sites (e.g., at a restriction enzyme site or polylinker) and operably linked to different regulatory sequences. For example, a site for insertion can be the viral enhancer/promoter proximal site (i.e., 5'LTR-driven gene locus). Alternatively, the desired sequences can be inserted into the viral promoter distal site, where the expression of the desired sequence or sequences is through splicing of the promoter proximal cistron, an internal heterologous promoter as SV40 or CMV, or an internal ribosome entry site (IRES).

The retroviral vectors of the invention may additionally include a marker sequence(s) or marker gene(s) which encode(s) a protein conferring antibiotic resistance or which provide a molecular tag on transduced cells to permit their isolation by positive selection or by cell sorting devices. Examples of antibiotic resistance include the aminoglycoside phosphotransferase gene which is encoded by neo (aph) and confers resistance to neomycin or G418 (see e.g., Southern, J. Mol. Appl. Gen. 1:327(1982)), and the hygromycin-B-phosphotransferase gene which is encoded by hyg (hph) and confers resistance to hygromycin-B (see e.g., Gritz, Gene 25:179(1983); Sugden, Mol. Cell. Biol. 5:410(1985); Palmer, Proc. Natl. Acad. Sci. USA 84:1055 (1987)). Exemplary molecular tags include chimeric or wild type CD8 proteins and the nucleotide sequences encoding such proteins.

Nucleic acid molecules that encode the above-described substances, as well as other nucleic acid molecules that are advantageous for use within the present invention, may be readily obtained from a variety of sources, including for example depositories such as the American Type Culture Collection (ATCC, Rockville, Md.), or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No. 67024 (which contains a sequence which encodes Interleukin-1b), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

Alternatively, cDNA sequences for use with the present invention may be obtained from cells which express or contain the sequences. Briefly, within one embodiment mRNA from a cell which expresses the gene of interest is reverse transcribed with reverse transcriptase using oligo dT or random primers. The single stranded cDNA may then be amplified by PCR (see e.g., U.S. Pat. Nos. 4,683,202, 4,683,195 and 4,800,159; PCR Technology: Principles and Applications for DNA Amplification, Erlich (ed.), Stockton Press, 1989)) utilizing oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA. Nucleic acid molecules which are carried and/or expressed by the recombinant retroviruses described herein may also be synthesized, for example, on an Applied Biosystems Inc. DNA synthesizer (e.g., APB DNA synthesizer model 392 (Foster City, Calif.).

The following examples are presented to illustrate the present invention and to assist one of ordinary skill in making and using the same. The examples are not intended in any way to limit the scope of the invention.

EXAMPLES

The examples demonstrate that gp64 can efficiently pseudotype retroviral vectors to high titer without the cellular cytotoxicity and other disadvantages associated with retroviral vectors pseudotyped with VSV-G. This approach is advantageous over existing approaches because narrow or tissue-specific tropism can be achieved. Thus, the present invention provides an improved approach to pseudotyping over existing approaches, particularly those employing VSV-G.

The results of the experiments conducted in the following examples show that gp64 confers high titer to pseudotyped vector particles and that gp64 protein can be stably expressed in packaging cell lines. An extensive analysis of gp64 cell and species tropism was performed in vitro using 24 different target cell lines and the sensitivity of gp64-pseudotyped vectors to human complement inactivation was determined. Also the production of gp64 pseudotyped vectors was scaled up and the binding and elution properties of these vectors was determined during particle purification by anion exchange chromatography. Further, two distinct experiments were performed to analyze the in vivo transduction efficiency of gp64-pseudotyped vectors. The following examples show that the pseudotyped retrovirus of the present invention, pseudotyped with baculovirus gp64 envelope protein, confer efficient gene transfer in vivo and that the pseudotyped retrovirus are complement resistant in animal models and have a tropism restricted against hematopoietic cells including human dendritic cells, Example 1

Preparation and Production of Recombinant 3rd Generation Pseudotyped Lentiviral Vectors In contrast to existing pseudotyped vectors, the present examples employ gp64 in pseudotyping third-generation HIV lentiviral vectors (see e.g., Kumar et al., Hum. Gene Ther. (2003) 14:67–77). The pseudotyped third-generation HIV vectors employed in these examples have three additional HIV genes deleted (tat, nef and vpu) and the vector is produced through expression of Rev protein in trans (see e.g., Dull et al., (1998) J.Virol., 72:8463–8471).

The VSV-G and baculovirus (AcNPV) gp64 envelope genes were subcloned into a mammalian expression vector (pMD-2) that carries a CMV promoter, a β-globin intron upstream of the ORF and a β-globin poly A signal (see e.g., Dull et al., (1998) J.Virol., 72:8463–8471). The VSV-G ORF fragment was removed by EcoRI digestion of pMD.G (see e.g., Ory et al., Proc. Natl. Acad. Sci. USA (1996) 93:11400–11406) with EcoRI and ligated into EcoRI digested pMDLg/pRRE (see e.g., Dull et al., (1998) J.Virol., 72:8463–8471) to produce pMD2-VSVG-Envelope (pCG909). The gp64 ORF fragment was prepared by PCR amplification of the AcNPV envelope region from BacPak6 (Clontech, Palo Alto, Calif.) with addition of EcoRI sites at each end. The primers used for amplification are as follows: Forward Primer 5'-acctgggaattcgccgccac catgctactagtaaatcagtcacaccaa-3' (SEQ ID NO: 1; adds an EcoRI site and a Kozak consensus sequence upstream of the ATG); Reverse Primer 5'-actgacgaattcttaatattgtctattac-ggtttcta'3' (SEQ ID NO: 2; adds an EcoRI site downstream of the stop codon). PCR amplification using these primers produced a product of 1.6 kb. The PCR product was digested with EcoRI and ligated into EcoRI cut pMDLg/p.RRE to produce pMD2-AcNPV-Envelope (pCG917). For both VSV-G and gp64, the resulting plasmids were confirmed by sequencing.

Small-scale production of the pseudotyped vectors employed in the present examples were produced by transient transfection according to published procedures (see e.g., Dull et al., (1998) J.Virol., 72:8463–8471) using a mixture of four plasmids in the following amounts per 10 cm dish: pMDLg/pRRE (Gag/Pol expression plasmid) at 6.5 μg, pRSV-Rev (see e.g., Dull et al., (1998) J.Virol., 72:8463–8471) at 2.5 μg, Transfer Vector (pRRL.sin.CMV.eGFP.ppt.pre or pRRL.sin.CMV.eGFP.pre) (see e.g., Follenzi et al., Hum. Gen. Ther. (2002) 13:243–260) at 10 μg, and 3.5 μg of envelope plasmid (pMD2.VSVG-Envelope or pMD2.AcNPV.Envelope or pMD2.Ampho.Env, see e.g., Fine et al., Blood (1994) 83:43–50). Vector particles were harvested in conditioned medium in one 24-hour collection. Vectors were concentrated by ultracentrifugation in a SW28 swinging bucket rotor at 19,500 rpm for 2 hr 20 min. Titer analysis and determination of p24$^{Gag}$ concentration were performed as previously described (see e.g., Dull et al., (1998) J.Virol., 72:8463–8471).

Large-scale production of pseudotyped vectors employed in the present examples were produced by transient transfection in 10-stack cell factories (Nunc, Rochester, N.Y.) as follows: low passage 293T cells were expanded and seeded at 5.75×10$^8$ cells per cell factory the day prior to transfection. The following day, the medium on the cells was changed 2 hours prior to transfection. Four plasmids were co-transfected in the following amounts per cell factory: pMDLg/p.RRE at 747.5 μg, pRSV-Rev at 287.5 μg, Transfer Vector (pRRL.sin.CMV.eGFP.ppt.pre or pRRL.sin.CM-V.eGFP.pre or pRRL.sin.CMV.hFIX.ppt.pre) (see e.g., Tsui et al. Nat. Biotechnol. (2002) 20:53–57) at 1.15 mg, and 402.5 μg of envelope plasmid (pMD2.VSVG-Envelope or pMD2.AcNPV.Envelope or pMD2.Ampho.Env).

For each cell factory, the DNA was mixed with 0.1×TE to a final volume of 51.75 ml. Next, 5.75 ml of 2.5M CaCl$_2$ was added and mixed. This mixture was then added to 57.5 ml of 2×HBS and added to the ten-stack. Medium was changed 16 hours later and conditioned medium containing vector particles was harvested in two collections at 24 and 48 hrs after the medium change. Vectors were purified by DEAE ion exchange (ToyoPearl DEAE-650C) chromatography by loading the conditioned medium at a 20:1 ratio of load volume to bed volume. The column was then washed with 5 volumes of PBS and eluted with 2.5 volumes of PBS containing 0.75M NaCl. The eluate was further concentrated by ultracentrifugation as for small-scale vector preparations. For the human Factor IX vectors that were injected into mice, transducing units were calculated based on the p24$^{Gag}$ concentration and the average infectivity (in TU/ng p24$^{Gag}$) determined for GFP vectors with the same pseudotypes.

Titers were determined by infecting target cells in a 6-well plate format: 5×10$^4$ cells per well (2×10$^5$ cells per well for HuH7 hepatoma cells) were seeded 24 hours prior to infection. Vector-containing medium was serially diluted 10-fold in culture medium and 1 ml of diluted vector was used to infect 1 well of target cells in the presence of Polybrene (8 μg/ml) in 2 ml total volume. Medium on the infected cells was changed 24 hours later. After another 48 hours, transduced cells were harvested by trypsinization and resuspension in 1 ml medium. Cells were pelleted by centrifugation in a clinical centrifuge for 2 min and resuspended in fixing medium: PBS+1% Formaldehyde (Sigma). Cells were stored at 4° C. until FACS analysis for % GFP-positive cells using a Becton-Dickinson FACSort. Titer was calculated with the following formula: % GFP positive cells/100×cell number (1×10$^5$ for 293T and HeLa cells; 2×10$^5$ for HuH7 cells)×dilution factor=infectious units/ml. (Only percentages less than 25% were used because FACS analysis is not linear over 25%.)

p24 antigen concentration was determined using an ELISA kit (Alliance, NEN-Dupont). Infectivity was determined using the following formula: Titer (in infectious units/ml) divided by p24 concentration (in ng/ml)= infectious units/ng p24.

Example 2

Determining Whether Baculovirus gp64 Envelope Protein Confers High Infectivity to 3rd Generation HIV-1 Lentiviral Vectors To determine whether gp64 could pseudotype the more advanced HIV vector of the present invention, pseudotyped HIV vector particles were prepared and tested for their ability to transduce three human cell lines. Several independent batches of third generation HIV-1 vector particles carrying the gene encoding Green Fluorescent Protein (GFP) were prepared by transient transfection and pseudotyped with the VSV-G envelope glycoprotein or baculovirus gp64. The unconcentrated conditioned medium from the transfected cells was tested for infectious titer using 293T, HuH7 human hepatoma and HeLa cells as targets (FIG. 1a).

Figure 2:
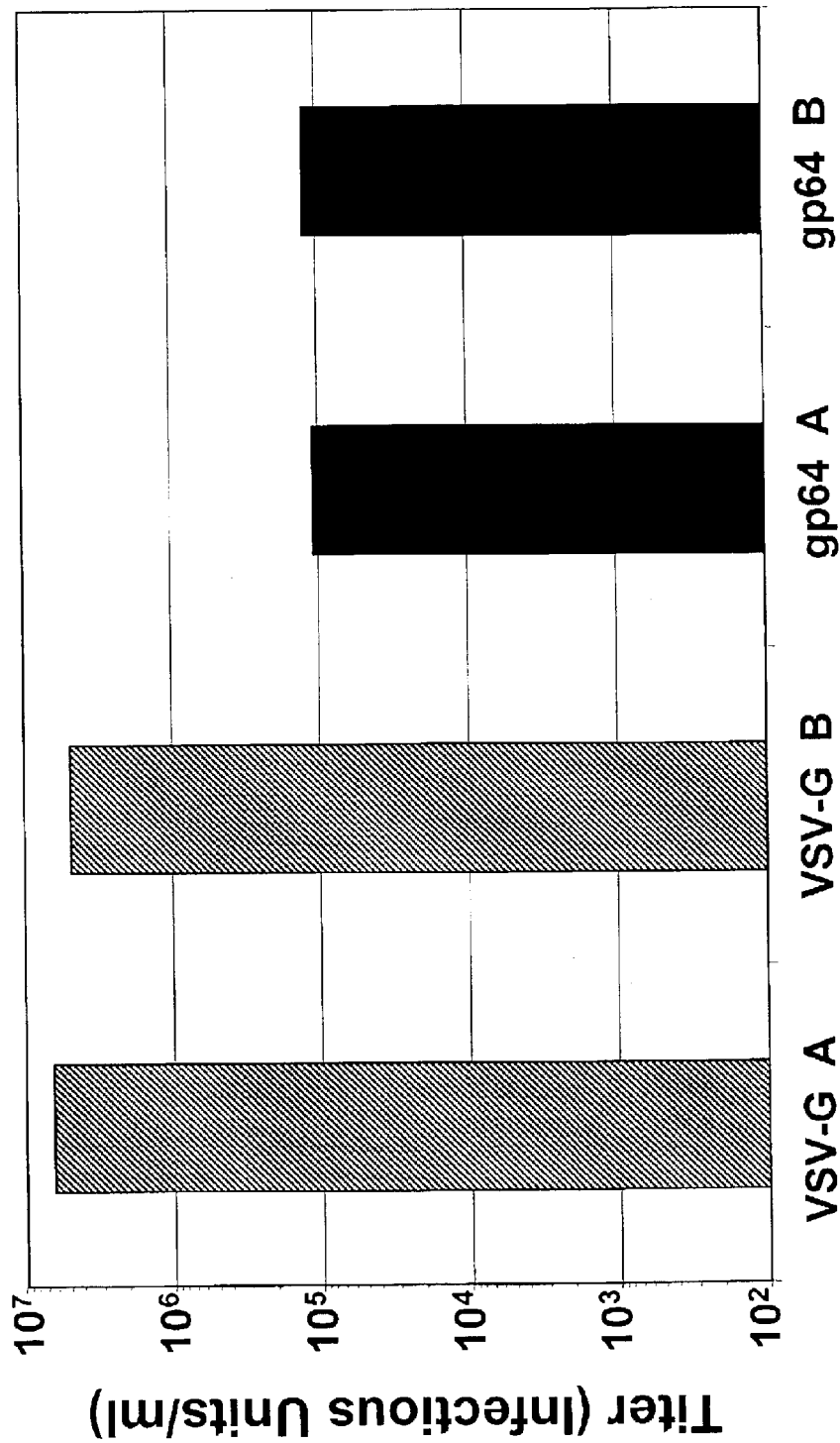
FIG. 2 is a bar graph showing a titer comparison of VSV-G and gp64-pseudotyped retroviral vectors (MLV-based) on 293T cells. Duplicate preparations (A and B) of MLV-based retroviral vectors carrying a GFP transgene were generated by transient transfection and pseudotyped with either the VSV-G (hatched bars) or gp64 envelope glycoprotein (black bars). These preparations were assayed for endpoint titers on 293T target cells. Titer values (infectious units/ml) were calculated based on % GFP positive cells as determined by FACS analysis.

The results in this example, demonstrate that gp64-pseudotyped vector was infectious on all three cell lines, with average titers ranging from $8.1 \times 10^4$ transducing units (TU)/ml to $1.2 \times 10^6$ TU/ml. The titers of the VSV-G-pseudotyped vectors ranged from $7.8 \times 10^5$ TU/ml to $4 \times 10^6$ TU/ml on the same cell types. The gp64-pseudotyped vector titers were down 25-fold on 293T cells compared to VSV-G but were only 3-fold lower than VSV-G on HuH7 cells. The gp64 titer in HeLa cells was $9.3 \times 10^5$ TU/ml, higher than the VSV-G titer at $7.8 \times 10^5$ TU/ml. In addition, the results show that the gp64 envelope glycoprotein could also pseudotype an MLV-based oncoretroviral vector. gp64-pseudotyped MLV vectors were prepared and tested. The results show that the titer on 293T cells was in the high $10^4$ range (FIG. 2), which is similar to the 293T titer determined for lentiviral vectors pseudotyped with gp64 (FIG. 1a).

To investigate possible variations in total particle production, the p24$^{Gag}$ protein levels were quantitated by ELISA and the infectious titer values were normalized to ng of p24$^{Gag}$ to give the infectivity (TU/ng p24$^{Gag}$), which reflects the ratio of infectious particles to total particles (FIG. 1b). The p24$^{Gag}$ levels in the preparations of gp64-pseudotyped particles were generally lower than those for VSV-G-pseudotyped particles, a phenomenon that seemed to be specific to transient expression of gp64 protein. On comparing these normalized values for the two vectors, it was shown that gp64 vector infectivity was 8-fold lower than VSV-G on 293T cells but there was no significant difference between their infectivities on HuH7 and HeLa target cells.

Pseudotransduction is where transduction using pseudotyped vector particles results in the detection of cells that appear positive for a protein encoded by the pseudotyped vector due to carryover of this protein from the transfected producer cells, instead of integration of the transduced vector genome (see e.g., Gallardro et al, Blood (1997) 90:952–957; Liu et al., J. Virol. (1996) 70:2497–2502). To test the possibility of pseudotransduction using the vectors of the present invention, gp64 vector-transduced cells were passaged and transgene expression examined after two weeks in culture. If pseudotransduction occurred then cells that were pseudotransduced would show a decrease over time in percent GFP positive cells and in GFP fluorescence intensity due to degradation of the GFP protein. In contrast, the results show of these experiments show that VSV-G and gp64 vector transduced cells maintained the same percentage of GFP-positive cells over this time period and in both cases the GFP fluorescence intensity increased over time (Table 1). Thus, the detection of GFP was not due to pseudotransduction and was due to transduction of the cells with the viral vector genome encoding GFP.

Figure 3:
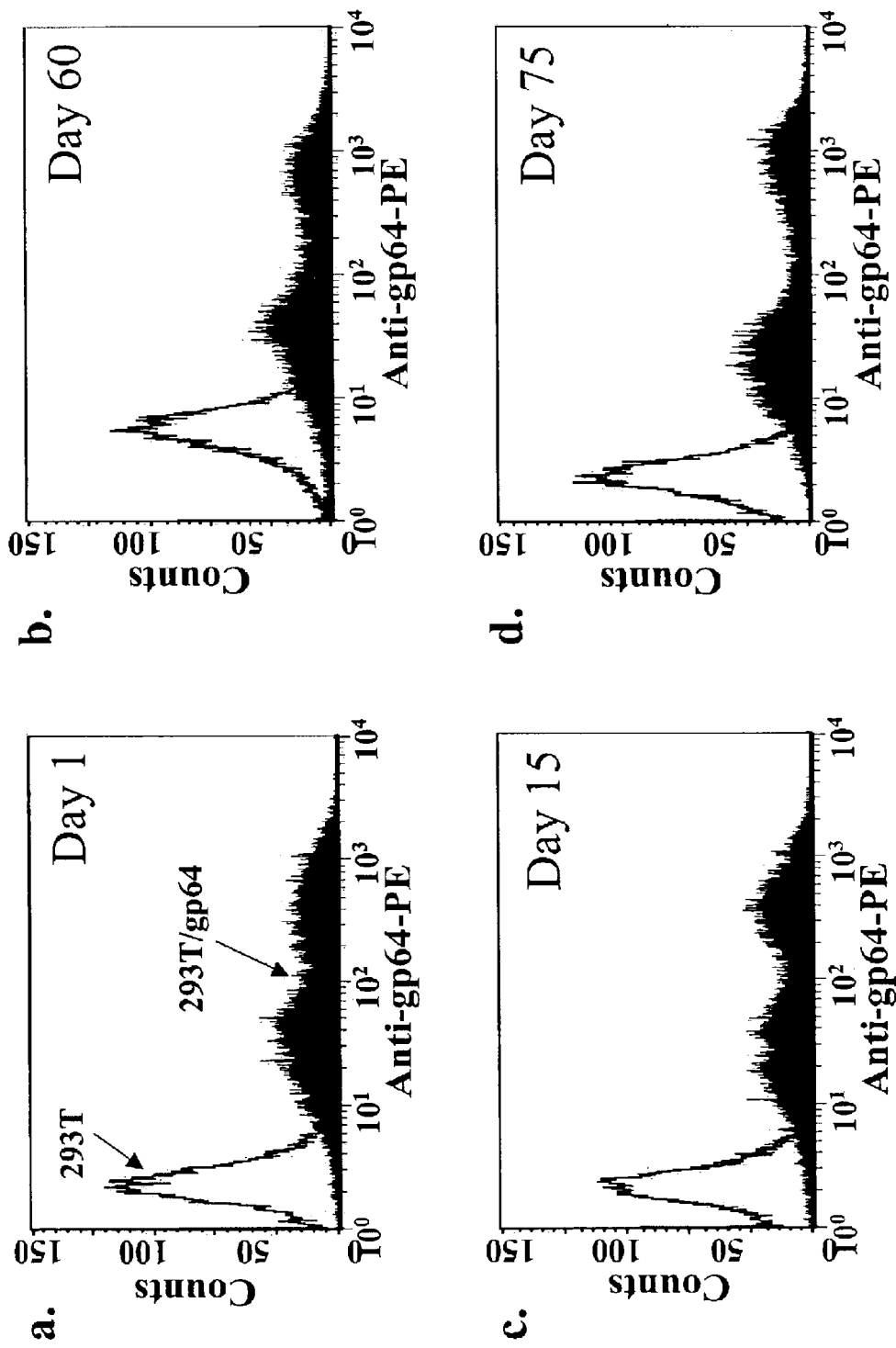
FIGS. 3a–d are histogram plots of fluorescence intensity (X axis) versus counts (Y axis) showing that gp64 can be stably expressed at high levels for prolonged passage in culture without signs of cytotoxicity. A 293T cell line stably expressing gp64 (293T/gp64) was generated by co-transfection of a plasmid containing a CMV-gp64 cassette with a second plasmid containing the hygromycin selectable marker followed by selection in hygromycin and FACS sorting to enrich for the top 10% of gp64-expressing cells in the population. The resulting 293T/gp64 cells and a gp64-negative cell line (293T) were passaged in culture over 75 days. At 15-day intervals, cells from each culture were stained using a primary anti-gp64 antibody and a secondary antibody conjugated to phycoerythrin (PE). Cells were analyzed by FACS and results from culture days 1, 15, 60 and 75 are shown as histogram plots (FIGS. 3a, b, c, d, respectively) of PE fluorescence intensity (X-axis) versus counts (Y-axis). The 293T negative cells are denoted by the white-filled curves while the 293T/gp64 cells are represented by the black-filled curves.

Also, a 293T cell line that constitutively expressed gp64 was also generated and it was shown that the surface expression of the protein was stable over 10 weeks (25 passages) in culture. The cell line showed no evidence of syncytium formation or cytotoxicity (FIG. 3), indicating that gp64 would be amenable to use in a stable constitutive packaging or producer cell line.

Example 3

Comparing gp64 and VSV-G Infectivities on Various Cell Lines In Vitro

To fully exploit the utility of the present invention in gene therapy applications, the tissue and species tropisms of different envelope glycoproteins were assessed. In particular, various envelope pseudotypes were investigated to determine whether they can mediate entry into the cell types of interest and whether the envelope can mediate transduction of human cells as well as cells derived from relevant animal models. As a step toward analyzing the tropism of gp64-pseudotyped lentiviral vectors, the infectivity of these pseudotypes on a variety of cell lines was determined in vitro.

Figure 4:
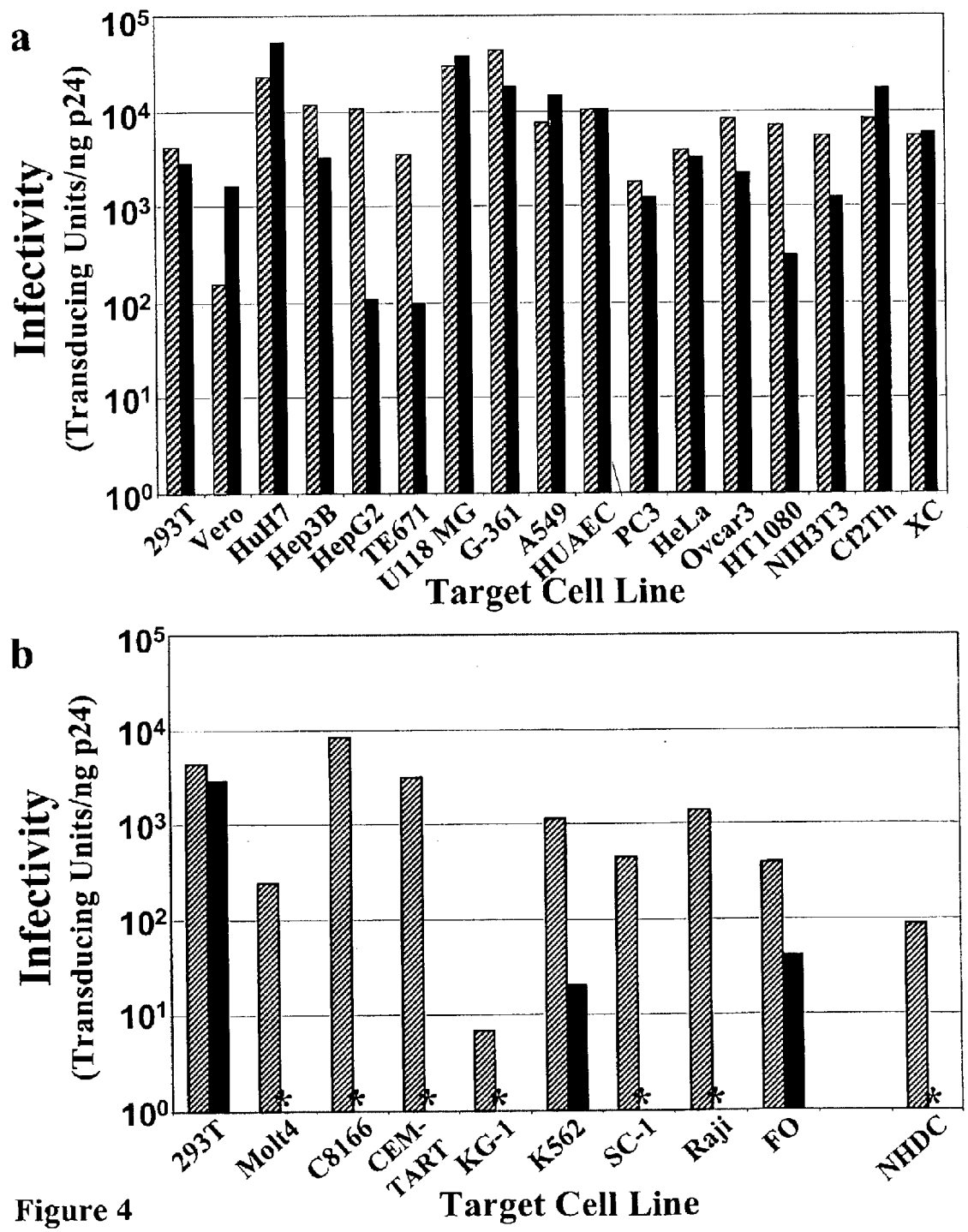
FIGS. 4a–b are bar graphs showing VSV-G and gp64 pseudotype infectivities on various target cell lines. Preparations of lentiviral vectors carrying the GFP transgene and pseudotyped with VSV-G (hatched bars) or gp64 envelope glycoprotein (black bars) were prepared by transient transfection followed by concentration by ultracentrifugation. The vectors were serially diluted and used to infect the various target cell lines indicated on the X-axis. FACS analysis was used to determine the percentage of GFP expressing cells and endpoint titer values were calculated. The titer values were normalized to ng of p24$^{Gag}$ in the preparations to yield infectivity values in transducing units/ng p24$^{Gag}$ for each pseudotype and cell line. The cell lines represented in FIG. 4a are as follows: 293T (human embryonic kidney), Vero (African Green Monkey kidney), HuH7 (human hepatoma), Hep3B and HepG2 (human hepatocellular carcinomas), Te671 (human rhabdomyosarcoma), U-118 MG (human glioblastoma), G-361 (human melanoma), A549 (human lung carcinoma), HUAEC (human umbilical arterial endothelium), PC-3 (human prostate carcinoma), HeLa (human cervical carcinoma), Ovcar-3 (human ovarian carcinoma), HT-1080 (human osteosarcoma), NIH/3T3 (mouse embryonic fibroblasts), Cf2Th (canine thymus) and XC (rat epithelial cells). Hematopoietic cells analyzed in FIG. 4b are: MOLT-4, C8166 and CEM-TART (all human T lymphocytes), KG-1 (human myeloblasts), K-562 (human promyelocytes), SC-1 and Raji (human B lymphocytes), FO (mouse B lymphocytes) and NHDC (human primary normal dendritic cells). Asterisks indicate instances of undetectable infectivity with the limit of detection at 1.0 transducing unit/ng p24.

Preparations of VSV-G and gp64-pseudotyped lentiviral vectors carrying a CMV-GFP. transgene cassette were generated by transient transfection and concentrated 100-fold by ultracentrifugation. The results of these experiments showed that gp64-pseudotyped vectors could be ultracentrifuged with no substantial loss of titer or p24$^{Gag}$ and no change in the vector infectivities (Table 2). The concentrated vector preps were analyzed for p24$^{Gag}$ concentration and then tested for end point titers on a variety of cell lines. Infectivity values were calculated by dividing the titer value by the p24$^{Gag}$ concentration (FIG. 4). The infectivity values for VSV-G and gp64 using 293T, HuH7 and HeLa target cells were slightly different from those determined in separate experiments (see FIG. 1). These small disparities are most likely due to slight differences in the vector preparations and the typical variation of the titer assay, and not due to concentration since average infectivities of unconcentrated and concentrated preps were similar.

These results of these experiments also show that the gp64 infectivity was equivalent or better than VSV-G infectivity on a number of cell lines (FIG. 4a) including Vero, HuH7, U-118 MG, A549, HUAEC, Cf2Th and XC cells. Relative infectivity for gp64 pseudotypes was slightly reduced (less than 10-fold lower than VSV-G) on 293T, Hep3B, G-361, PC-3, HeLa, Ovcar-3 and NIH/3T3 cells. However, there were several cell lines such as HepG2, Te671 and HT-1080 where gp64 pseudotype infectivity was greater than 10-fold lower than VSV-G.

Notably, very low infectivity for gp64 pseudotypes was observed in cells of hematopoietic origin (FIG. 4b). Initially, no detectable transduced cells were detected when gp64-pseudotyped vector was used to infect MOLT-4, C8166 and CEM-TART cells (all human T lymphocyte cell lines). The same vector preps were used for titrations on all of the cell lines in FIG. 4, indicating that the lack of transduction on hematopoietic cells was not due to lack of active vector particles. Subsequently, other hematopoietic cell types were examined and found that there was no detectable infectivity for gp64 vector on KG-1 human myeloblasts or on Raji and SC-1 human B lymphocytes and extremely low infectivity on the K-562 human erythroleukemia cells and FO mouse B lymphocyte cells.

Finally, the infectivity on dendritic cells was analyzed. Published reports indicated that VSV-G mediated transduction of APC's such as dendritic cells may contribute to immune responses against the transgene product or vector (Metharom et al., Hum. Gene Ther. (2001) 12:2203–2213; Gruber et al., Blood (2000) 96:1327–1333). In this analysis, primary normal human dendritic cells (NHDC) were obtained and transduced them with the VSV-G and gp64 vectors. Again, there was no detectable transduction activity for the gp64 vector using these target cells whereas the VSV-G pseudotyped vectors transduced the NHDC at 100 times the limit of detection.

Thus, gp64 showed notably reduced infectivity in a number of cell types, but was especially inefficient at transducing cells of hematopoietic origin including human T lymphocytes and primary human dendritic cells. This profile demonstrates that gp64 has a more restricted set of cell types that it can efficiently transduce compared to VSV-G. On the other hand, gp64 infectivity levels were similar to those of VSV-G on many cell lines, suggesting that gp64 pseudotyping might be a useful alternative for transduction of many target tissues.

Example 4

Determining Whether gp64-pseudotyped Lentiviral Vectors Efficiently Transduce Mouse Cells In Vivo Although gp64-pseudotyped lentiviral vectors are able to efficiently transduce a number of cell lines in vitro, it was not known if the gp64 pseudotyped vectors could transduce cells in vivo and confer long-term gene expression. To determine for the first time whether gp64 could confer significant infectivity in vivo, gene transfer in mice was investigated after injection of pseudotyped lentiviral vectors. An initial mouse experiment was designed using human Factor IX as the reporter transgene to facilitate detection of any transduction and transgene expression. Factor IX is easily quantitated and can be detected in the blood following secretion from many tissues (High, K. A., Circ. Res. (2001) 88:137–144). In addition, because the in vivo tissue tropism for gp64 was unknown, the constitutive CMV promoter was used to drive Factor IX expression and to avoid problems of tissue-specific expression.

To generate vectors for injection into mice, the production of the vector was scaled up from 10 cm dishes into cell factories and large-scale transient transfections were performed in ten-stacks. Three lentiviral vector preparations carrying the CMV-human Factor IX transgene cassette and pseudotyped with VSV-G, gp64 or the MLV amphotropic envelope (Ampho) were produced in this manner. The vector particles from all three preparations were then purified by anion exchange chromatography. Both the gp64 and Ampho-pseudotyped vector particles bound to and eluted from the DEAE column under the same conditions as the VSV-G pseudotypes and 100% of the input vector was recovered using this process (Data not shown).

Figure 5:
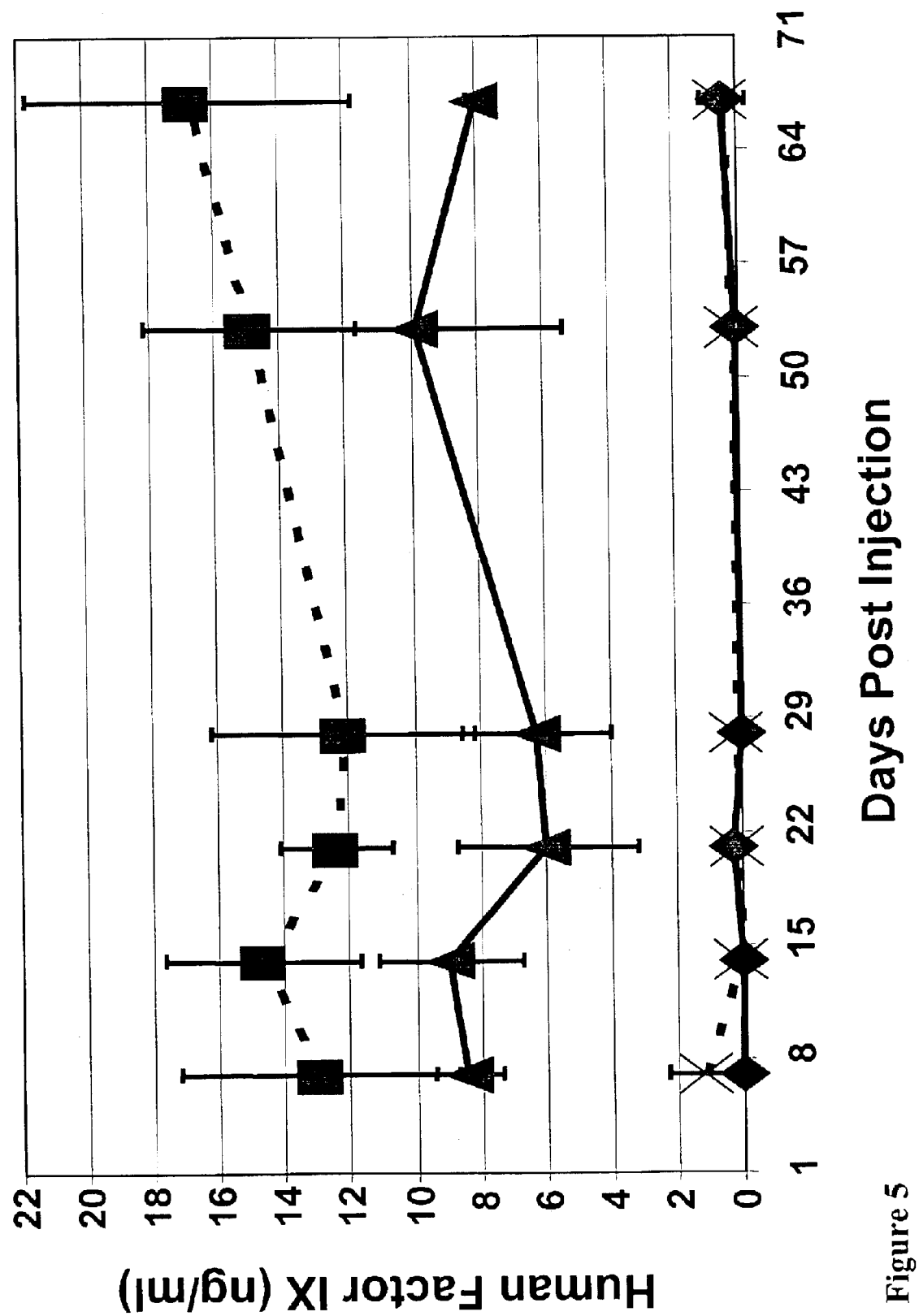
FIG. 5 is a line graph showing the expression of human Factor IX in Swiss Nude mice following injection with pseudotyped lentiviral vectors. Preparations of lentiviral vectors carrying a CMV driven human Factor IX transgene and pseudotyped with the VSV-G, gp64 or MLV amphotropic envelope glycoproteins were produced by large-scale transient transfection followed by purification and concentration. These preparations were tested for p24$^{Gag}$ concentration and infectivity was confirmed using 293T cells in vitro. 100 μl of each vector preparation or 100 μl of PBS as a negative control was injected into each of three NIH Swiss Nude mice. The final doses of transducing units (TU) determined using 293T target cells were: 5.8×10$^7$ TU for VSV-G, $1.8 \times 10^7$ TU for gp64 and $1.7 \times 10^7$ TU for the Ampho vector. Blood was collected from the injected mice at time-points after injection as indicated on the X-axis. The concentration of human Factor IX in the mouse serum was determined by ELISA. The data points indicate the average human Factor IX concentration in the three mice with the corresponding standard deviations. The key to the line graph symbols are as follows: VSV-G (squares with dashed line), gp64 (triangles with solid line), Ampho (X's with dashed line), PBS control (diamonds with solid line).

The final vector preparations were characterized by testing for $p24^{Gag}$ concentration and were confirmed to transduce 293T cells in vitro and express human Factor IX protein (data not shown). For each of the vectors, approximately 10 μg of $p24^{Gag}$ (or PBS as a negative control) was injected into Swiss Nude mice (3 mice per vector pseudotype) via a hepatic portal vein cannula. The doses in 293T transducing units (TU) for each vector were as follows: VSV-G mice received $5.8 \times 10^7$ TU, the gp64 mice received $1.8 \times 10^7$ TU and the Ampho mice were injected with $1.7 \times 10^7$ TU. Serum was collected from the mice at various time points after injection and analyzed for human Factor IX protein levels by ELISA (FIG. 5). The results of these experiments showed that the mice injected with PBS or the Ampho-pseudotyped lentiviral vector did not express any detectable Factor IX protein at any time point. The mice injected with VSV-G pseudotyped vector expressed detectable human Factor IX protein beginning at day 7 after injection and continuing at a stable level of 12–17 ng/ml for greater than 9 weeks. In contrast to the Ampho-pseudotyped vector but similar to VSV-G, the mice injected with the gp64-pseudotyped vector also expressed significant levels of human Factor IX. A stable level of 5–10 ng/ml human Factor IX was observed for more than 9 weeks in the gp64-injected mice. Thus, the mice injected with the gp64 pseudotyped vector expressed only slightly less Factor IX than the VSV-G vector injected mice, despite having received approximately 3-fold fewer transducing units.

The expression of human Factor IX in mice after injection with pseudotyped lentiviral vectors showed that the VSV-G and gp64 envelopes could confer efficient transfer of a gene into mouse cells in vivo. To determine whether liver cells in the mice were being transduced, mice were injected with pseudotyped vectors carrying a CMV-GFP transfer vector and liver sections of the injected mice were examined for GFP expression. A total of 12 Swiss Nude mice (3 mice per group) were injected via a hepatic portal vein cannula with PBS or with lentiviral vectors carrying the CMV-GFP gene cassette and pseudotyped with VSV-G, gp64 or MLV Ampho envelope protein. The mice were injected with approximately 10 μg of $p_{24}^{Gag}$, which equated to $3.5 \times 10^8$ TU (using 293T cells as target cells) for the VSV-G vector, $1.3 \times 10^8$ TU for the gp64 vector and $1.7 \times 10^8$ TU for the Ampho vector. At day 11 post-injection, all twelve of the mice were sacrificed and their livers were removed, fixed and sectioned.

Figure 6:
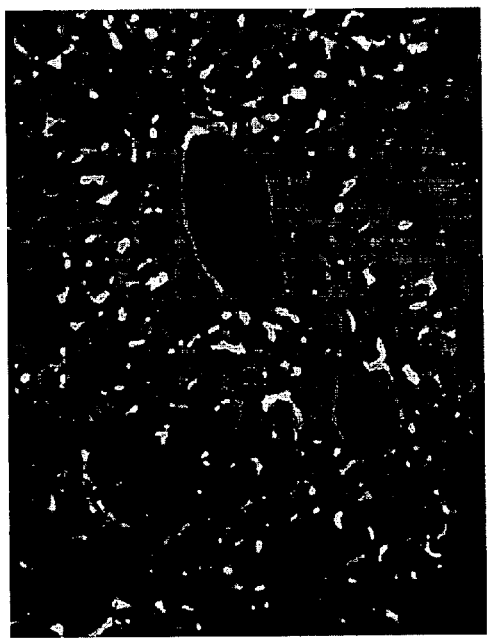
FIGS. 6a–d are photographs of mouse liver sections mounted on slides and imaged by fluorescent microscopy showing the expression of Green Fluorescent Protein (GFP) following injection with pseudotyped lentiviral vectors. Preparations of lentiviral vectors carrying a CMV-GFP transgene cassette and pseudotyped with the VSV-G, gp64 or MLV amphotropic envelope glycoproteins were produced by large-scale transient transfection followed by purification and concentration. These preparations were tested for $p24^{Gag}$ concentration and infectivity was determined using 293T target cells in vitro. 100 µl of each vector preparation or 100 µl of PBS as a negative control was injected into each of three NIH Swiss Nude mice via portal vein cannula. The final doses of transducing units (TU) determined using 293T target cells were: $3.5 \times 10^8$ TU for VSV-G, $1.3 \times 10^8$ TU for gp64 and $1.7 \times 10^8$ TU for the Ampho vector. At Day 11 after injection, mice were sacrificed and their livers were removed, fixed and sectioned. Liver sections were mounted on slides and imaged by fluorescence microscopy at 20× magnification.
Figure 6:
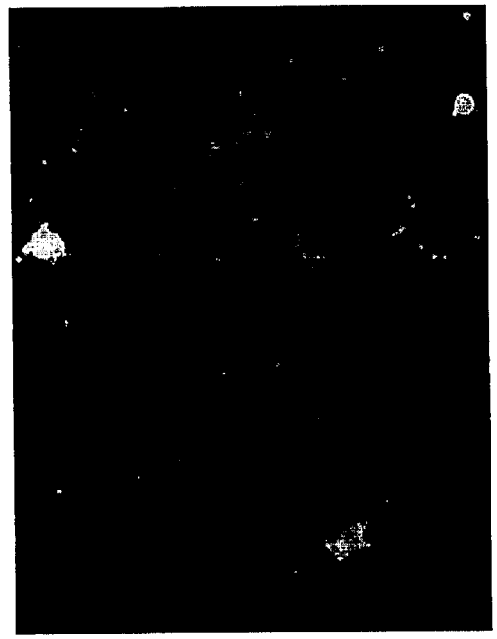
Figure 6:
Figure 6:
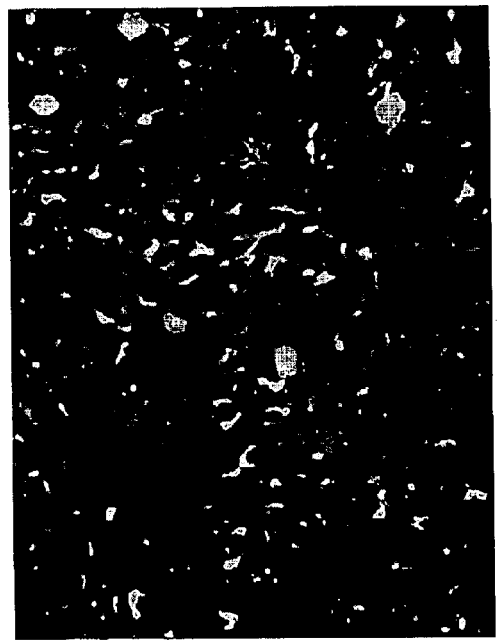

GFP expression was examined in the sections via fluorescence microscopy, and representative sections for each vector pseudotype are shown (FIG. 6). An independent veterinary pathologist analyzed the GFP expression patterns and cell morphology in a blind examination of the sections. The patterns of GFP expression were consistent throughout each liver and between the three mice in each group (data not shown). In both the mice injected with VSV-G pseudotyped vector and mice injected with gp64 vector, we saw that a substantial number of liver cells were positive for GFP. The majority of the positive cells in both experimental groups were non-parenchymal cells (possibly Kupffer or sinusoidal cells) while a few of the green cells were hepatocytes (FIG. 6b). The gp64 mice also showed a slightly greater number of GFP-positive hepatocytes compared to VSV-G (FIGS. 6b and c). Interestingly, approximately the same number of liver cells was positive in the VSV-G and gp64 mice despite the injection of less than half as many 293T-transducing units in the gp64 vector dose. Finally, very few GFP-positive cells were observed in the livers of the Ampho vector treated mice. An intriguing feature in the Ampho-transduced livers was that virtually all of the positive cells were hepatocytes (FIG. 6d). In both the Factor IX and GFP experiments, VSV-G and gp64 showed similar and significant expression with notably lower or undetectable expression in the Ampho vector treated mice.

Example 5

Determining Whether gp64-pseudotyped Vector Particles are Sensitive to Inactivation by Human Serum Complement Lentiviral vectors pseudotyped with VSV-G but not Ampho envelope are sensitive to inactivation by human serum complement (DePolo, N.J., Mol. Ther. (2000) 2:218–222). To determine whether gp64-pseudotyped lentiviral particles are resistant or sensitive to complement, human, rat and mouse serum was used to test the complement-inactivation of gp64-pseudotyped vector preparations. VSV-G and gp64-pseudotyped lentiviral vectors carrying the GFP transgene were produced by transient transfection in 293T cells and concentrated 100-fold by ultracentrifugation. Titers were determined using 293T cells as targets and the vector preps were normalized to a concentration of $10^6$ GFP TU/ml. The vector suspensions were diluted 1:5 into normal or heat-inactivated serum or into medium as a no-serum control. After incubation at 37° C. for one hour, the reactions were diluted and used to infect 293T target cells to determine end point titers. The titer of the no-serum control samples were calculated and set as 100% recovery of titer for the reaction. The titer of samples exposed to serum is reported as a fraction of the 100% control sample. The results of these experiments showed that, in human serum (FIG. 7a, left), VSV-G pseudotypes were sensitive to inactivation, with complement-active serum causing 30 to 100-fold reduction in titer. Likewise, the gp64-pseudotyped lentiviral vector was also sensitive to inactivation by the human sera. 20 to 50-fold reductions in titer were observed for gp64 pseudotypes in serum from the same donors (FIG. 7b, right). The human serum samples were tested for hemolytic complement activity ($CH_{50}$) and all were found to be in the normal range (data not shown).

The gp64-pseudotyped particles were also tested to determine if they would be inactivated by serum from mice and rats. It has been reported that baculovirus vectors produced in insect cells are sensitive to substantial inactivation in vitro by human, rat and guinea pig serum and that the vectors have extremely poor infectivity in vivo in mice and rats due to complement inactivation (see e.g., Hofmann et al., Gene Ther. (1998) 5:531–536; Sarkis et al., Proc. Natl. Acad. Sci. USA (2000) 97:14638–14643; Huser et al., Nat. Biotechnol. (2001) 19:451–455. Thus, the gp64-pseudotyped lentiviral vectors of the present examples were further tested in order to distinguish whether the complement sensitivity of baculovirus vectors in rodent serum is due to recognition of the specific envelope glycoprotein or the insect-derived lipid envelope. The results of these experiments showed that the gp64-pseudotyped lentiviral vectors were not inactivated by serum from C57BL/6 mice or Nude rats (FIG. 7b). Neither the pooled serum from C57BL/6 mice (2 mouse sera per pool) nor the serum from a single donor rat caused more than a four-fold reduction in titer, unlike the more severe inactivation observed in human serum (FIG. 7a). VSV-G and Ampho pseudotyped vectors were also resistant to inactivation by both the mouse and rat sera (data not shown). Thus, like VSV-G, the gp64 envelope glycoprotein makes lentiviral vectors sensitive to inactivation by human serum but not by mouse or rat serum.

Example 6

Determining whether 293T Cells are stably transduced or pseudotransduced by VSV-G and gp64-pseudotyped lentiviral vectors It has previously been shown that certain viruses and viral vectors can carry proteins as they bud from the producer cell and infect a new host cell. In many instances, infection (transduction) of a host cell is determined by measuring the protein product of a reporter gene carried by the virus, such as GFP or LacZ. There are cases of viruses being falsely reported as infectious because transgene protein was measured in the target cell, but the protein was in that cell as a result of being carried by the virus particle and not as a result of viral genome integration and subsequent protein expression. This false assessment of infectivity is referred to as pseudotransduction.

Because of the possible problems related to pseudotransduction (which frequently are envelope protein-dependent), experiments were conducted to determine whether gp64-pseudotyped lentiviral vectors were mediating true transduction of target cells. One difference between stably transduced cells and pseudotransduced cells is that the quantity of protein in the cell should decrease over time in pseudotransduced cells as a result of protein degradation. In stably transduced cells, there should be no substantial decrease in protein levels because of the stable integration of the transgene and constant gene expression. To examine protein levels in transduced cells over time, populations of VSV-G and gp64 vector transduced cells were analyzed for GFP expression at the beginning (Day 3) and end of a two week period (Day 17). The populations of cells were generated by infecting 293T target cells with vector samples at two different dilutions differing by 10-fold concentration (1:25 and 1:250). (Assessment of % positive cells by FACS is only linear in the range of 0.1 to 25% positive, therefore the data were generated using cells infected with vector dilutions to fall into that range). At Day 3 and Day 17 the cell populations were analyzed by FACS, which provided quantitation of the % of GFP-positive cells as well as the average fluorescence in the positive population (i.e. the amount of GFP protein per positive cell).

The difference in % GFP positive cells between Day 3 and Day 17 for each population did not decrease substantially (largest decrease was 30%) (Table 1). In addition, the average fluorescence per cell (Mean Fluorescence, last column) actually increased over the two week period in all cases (Table 2). This indicates that the GFP-positive cells contained more GFP protein per cell on Day 17 than on Day 3. The increase in protein per cell, combined with the relatively stable percentage of positive cells in the population indicates that the protein is being expressed from a stably integrated GFP transgene. Therefore, the quantitation of positive cells at Day 3 of the assay is an accurate measure of the number of cells that are stably transduced as opposed to cells containing protein that was carried by the virus particles.

Example 7

Determining whether Gp64-pseudotyped lentiviral vectors survive concentration by ultracentrifugation Compared to other viral vectors such as adenovirus, retro and lentiviral vectors are produced at relatively low titers (infectious particles/ml). In order to increase the concentration of infectious particles, the viral particles can be pelleted by ultracentrifugation and resuspended in smaller volumes. This works well for many particles, including those pseudotyped with VSV-G, but has been problematic for particles pseudotyped with other envelope glycoproteins such as the MLV Amphotropic envelope (Ampho). The main problem in these cases is that one subunit of the Ampho envelope is removed during this ultracentrifugation process. Normally one subunit spans the membrane and is non-covalently attached to the second subunit, which is on the outer surface of the particle. The second outer subunit is required for virus attachment to the host cell receptor protein. It is the second outer subunit that is stripped during ultracentrifugation, the resulting particles are no longer infectious because they lack the ability to bind to their cognate receptors. Thus particles with certain envelope pseudotypes lose their infectivity upon centrifugation.

Because of the possible problems related to loss of infectivity following ultracentrifugation, experiments were conducted to determine whether gp64-pseudotyped lentiviral vectors could be concentrated using an ultracentrifuge process. Lentiviral particles were measured using two methods: p24 concentration and viral titer. p24 is a viral protein present in the capsid at a certain number of molecules per particle. The p24 concentration determined by ELISA is a measure of the total number of particles per unit volume. Because not all particles are infectious, we also determine the viral titer (infectious particles per unit volume). To determine whether virus particles can survive ultracentrifugation, we determine the p24 concentration and titer of vector preparations prior to and following the centrifuge step. In each case, the fold-concentration (last column) is determined by the change in volume of the preparation following centrifugation.

The results of these experiments show that both VSV-G and gp64-pseudotyped vector preparations were stable to ultracentrifugation because there was no significant decrease in p24 concentration or titer following concentration. In all cases, greater than 60% of the starting particles were recovered following centrifugation. The recovery of less than 100% of the particles may be due to variation in the p24 ELISA quantitation, which can vary from assay to assay up to 50%. In addition, the concentrated particles retained all of their infectivity as shown by the substantial recovery of titer following ultracentrifugation.

Discussion

The results of the experiments described in the above examples show the generally efficient ability of gp64,to pseudotype HIV vectors at high titers and, further, the high infectivity and pseudotyping ability of third generation lentiviral vectors lacking the HIV tat gene as well as all four HIV accessory genes. For gp64 pseudotyped vectors of the present invention, the infectivity on 293T cells was several fold lower than that of VSV-G pseudotypes, while it was very near or higher than the VSV-G infectivity on HuH7 and HeLa cells (FIG. 1b).

While the absolute titers (TU/ml) of gp64 pseudotyped lentiviral vectors were lower than for VSV-G vectors (FIG. 1a), this was generally due to lower particle production (lower $p24^{Gag}$ concentration) in the transiently produced gp64 vector preparations. This phenomenon can be overcome by producing vector particles in cells that were stably expressing gp64 or by inducing gene expression in transient producer cells using sodium butyrate (C. Schauber and M. Tuerk, unpublished observations). Further the results of the experiments provided herein show that gp64 could be used to pseudotype an MLV-based oncoretroviral vector and could confer titers in the same range as the pseudotyped lentiviral vectors (data not shown). Notably, this result shows that gp64 pseudotyping may be feasible with any member of the retrovirus family (Kumar et al., Hum. Gene Ther. (2003) 14:67–77).

The in vitro tropism shown in the experiments provided herein for gp64 suggests that gp64 pseudotyping can be advantageous for applications where tissues such as the liver, lung, skin, glia, endothelium or thymus are targets for transduction, because gp64 infectivity is high on cell lines derived from these tissues. In addition, infectivity greater than $10^3$ TU/ng p24 was observed for gp64 pseudotyped vectors on monkey cells (Vero), dog cells (Cf2Th), rat cells (XC) and mouse cells (NIH/3T3), indicating that gp64 can transduce cell types in several species that would be useful pre-clinical animal models (FIG. 4a).

Further, the results of the experiments described in the above examples show more extensive examination of 24 target cell types and indicate that gp64 infectivity varies more widely than that of VSV-G. The disparities in infectivity may be due to differences in the ability of the vector particles to bind to the target cells, implicating possible variations in the abundance of gp64 receptors on the different cell types. Different reports have suggested that phospholipid molecules including phophatidylinositol and phosphatidic acid as well as proteins are possible gp64 receptors (see e.g., Chernomordik et al., J. Virol. (1995) 69:3049–3058; Tani et al., Virology (2001) 279:343–353; Wickham et al., J. Gen. Virol. (1992) 73(12):3185–3194; Wang et al., J. Gen. Virol. (1997) 78(12):3081–3089). Alternatively, there may be differences in the membrane composition that affect the fusion of the viral membrane with the target cell membrane after binding has occurred. Indeed, membrane lipid composition has been shown to affect fusion mediated by gp64, probably as a result of differences in the shape of the fusion intermediate structures in the envelope (Chernomordik et al., J. Virol. (1995) 69:3049–3058).

Notably, the results of the experiments showed that gp64 pseudotyped lentiviral vectors were extremely inefficient at transducing human T lymphocyte cell lines as well as other hematopoietic cell types (FIG. 4b). This restriction against transduction of hematopoietic cell lines was also observed in published studies using baculovirus vectors, where K-562 and MOLT-4 cells as well as several other B and T lymphocyte cell lines were poorly infected with baculovirus (see e.g., Hofman et al., Proc. Natl. Acad. Sci. USA (1995) 92:10099–10103; Condreay et a., Proc. Natl. Acad. Sci. USA (1999) 96:127–132; Boyce et al., Proc. Natl. Acad. Sci. USA (1996) 93:2499–2504). However, the results also showed that gp64-pseudotyped vectors could not transduce primary human dendritic cells (NHDC) to any detectable level. Thus, the selective tropism of gp64 should prove to be highly beneficial in specific gene therapy applications.

It has been reported that lentiviral vectors pseudotyped with VSV-G can transduce human and mouse dendritic cells with high efficiency and induce humoral immune responses against transgene products (see e.g., Dyal et al., Blood (2001) 97:114–121; Metharom et al., Hum. Gene Ther. (2001) 12:2203–2213; Gruber et al., Blood (2000) 96:1327–1333). Also, VSV-G itself has been demonstrated to elicit antibody responses (see e.g., DePolo et al. Mol. Ther. (2000) 2:218–222; Charan et al. J. Virol. (1987) 61:2509–2514). The inability of gp64 pseudotypes to transduce dendritic cells provides a potential advantage over VSV-G because there could be a reduction in immune responses against the vector components or against the transgene products in vivo using gp64, After determining that the gp64-pseudotyped lentiviral vectors showed significant infectivity on a number of cell lines in vitro, experiments were conducted to confirm that the envelope could also confer infectivity in vivo. Production of vector preparations for these mouse studies required scale-up and purification of vectors with three different envelope glycoproteins. All three pseudotyped vectors were easily produced via transient transfection in ten-stack cell factories, demonstrating the ability to make gp64-pseudotyped vectors at large-scale without development of a stable cell line. Importantly, the results show that the identity of the envelope glycoprotein does not affect the binding or elution characteristics of the vector during purification by anion exchange chromatography. This discovery made vector purification simpler and preparations more uniform because all of the pseudotypes could be purified under the same conditions.

The results also showed that gp64-pseudotyped lentiviral vectors could efficiently transfer the human Factor IX gene or the GFP gene to mouse cells following portal vein injection (FIGS. 5 and 6). This finding is a significant departure from several published reports that baculovirus vectors are not infectious if injected into the vasculature of mice (see e.g., Sandig et al., Hum. Gene Ther. (1996) 7:1937–1945; Tani et al., Virology (2001) 279:343–353). For both the human Factor IX and GFP transgenes, the transduction efficiency and transgene expression of the gp64-pseudotyped vector was similar to that for VSV-G (see FIGS. 5, 6b and c), whereas there was significantly lower transduction observed in the Ampho vector injected mice (FIGS. 5 and 6d).

The selectivity of the Ampho-pseudotyped lentiviral vectors for transduction of hepatocytes was interesting and novel. Previous studies showed that the Ampho receptor, Pit2, should be highly expressed in liver tissue but the exact cell types of expression were not delineated (Kavanaugh et al., Proc. Natl. Acad. Sci. USA (1994) 91:7071–7075). Published reports have shown that retroviral vectors carrying the amphotropic envelope can transduce hepatocytes with high efficiency, but in most circumstances liver proliferation has been induced to overcome the cell cycle requirement of these vectors so the transduction patterns are not entirely dependent on the envelope (see e.g., Menoret et al., Hum. Gene Ther. (2002) 13:1383–1390; Xu et al., Mol. Ther. (2002) 5:141–153). Thus, the experiments described in the present examples are the first reported use of Ampho-pseudotyped lentiviral vectors in vivo and, despite the low transduction efficiency, demonstrates a previously unknown specificity of Ampho envelope for mouse hepatocytes in the absence of any liver proliferation.

Figure 7:
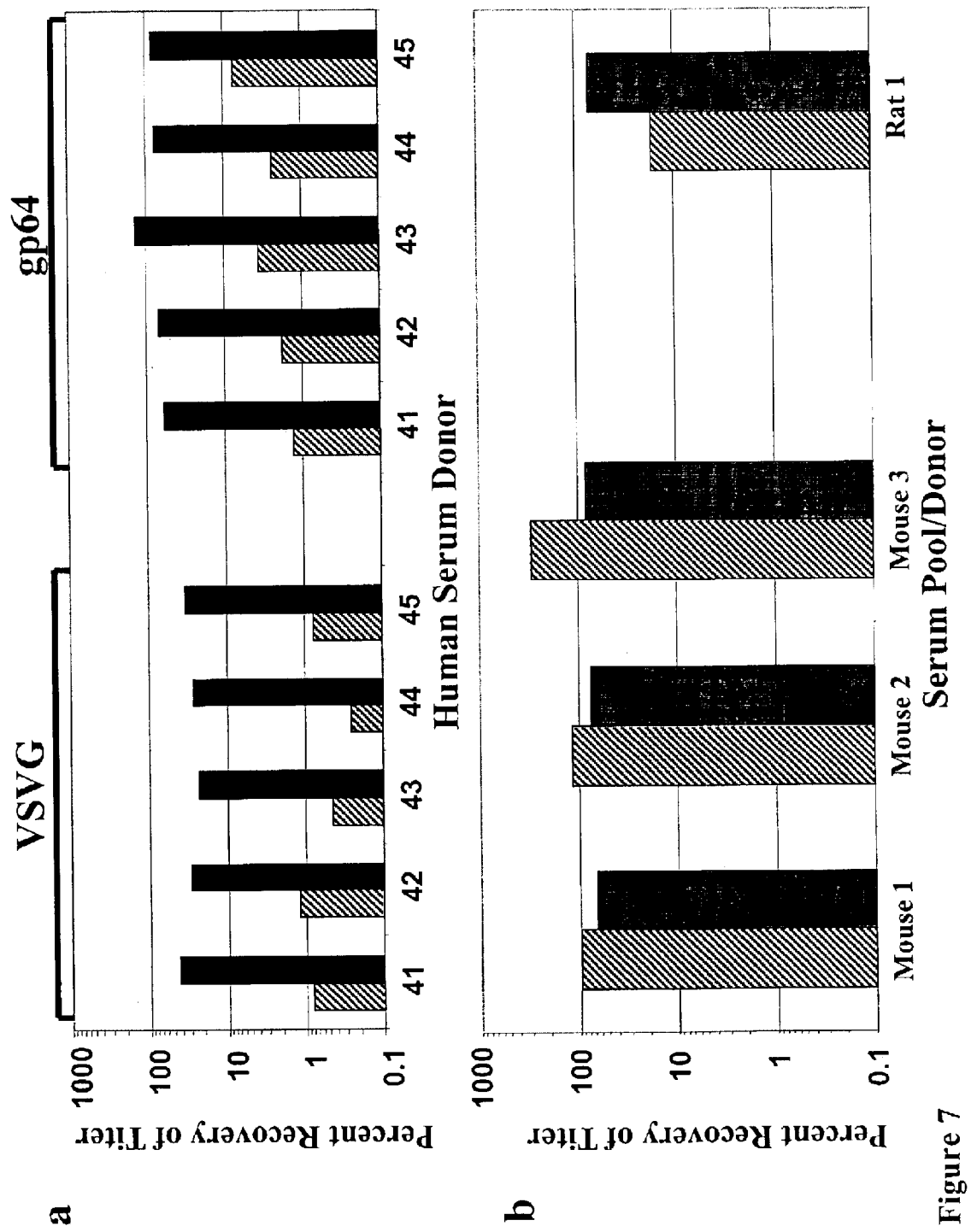
FIGS. 7a–b are bar graphs showing the complement sensitivity of gp64-pseudotyped lentiviral vectors in human, mouse and rat serum. For the assays depicted in FIG. 7a, concentrated preparations of lentiviral vectors carrying a GFP transgene and pseudotyped with VSV-G (left) or gp64 (right) envelope glycoprotein were normalized to a concentration of $10^6$ transducing units/ml. The vector was then diluted 1:5 into medium (the no-serum control) or human serum that was normal (hatched bars) or heat-inactivated (black bars) from 5 single human donors (denoted # 41–45). After a one-hour incubation at 37° C., the vectors were tested for end point titers on 293T cells. The titer from vector incubated with the medium control was set as 100% recovery of titer. The bars represent the percentage of titer remaining in the vector samples after incubation with normal or heat-inactivated serum compared to vector incubated with the medium control. For the assays depicted in FIG. 7b, gp64-pseudotyped lentiviral vectors were tested (as described above for FIG. 7a) for titer remaining after incubation with normal (hatched bars) or heat-inactivated (black bars) serum from C57/BL6 mice (3 pools of serum each from 2 mice; left) and one Nude rat (right).

A drawback of baculovirus vectors has been the inability to transduce cells in animal models in vivo because of complement inactivation. Along the same lines, it has been reported that the VSV-G envelope glycoprotein can make lentiviral vectors sensitive to human complement inactivation whereas Ampho-pseudotyped vectors are resistant. These findings evoked concern about complement inactivation of gp64-pseudotyped lentiviral vectors and prompted us to test them for sensitivity to complement from humans and rodents (FIG. 7). However, the results described in the present examples show that gp64 does indeed confer sensitivity to inactivation by human complement, but there was no sensitivity to complement from mice or rats. Because all of the vector pseudotypes (VSV-G, gp64 and Ampho) are produced in the same cell type, the resistance or sensitivity of the vectors is dependent on the identity of the envelope glycoprotein, and not a glycosylation characteristic of the membrane envelope derived from the producer cell. The sensitivity of gp64 to human complement inactivation can be avoided by directly injecting the vectors into specific tissues or through the use of complement regulatory proteins such as DAF (C. Schauber, manuscript in preparation).

In rodent serum, the results show that gp64-pseudotyped vectors are resistant to complement inactivation (FIG. 7b). This data is further confirmed the results of the mouse studies (FIGS. 5 and 6) showing that gp64 efficiently transduces murine cells following injection into the vasculature, contrary to the published reports that baculovirus vectors are sensitive to rodent sera and do not transduce cells in vivo after vascular injection. Therefore, it is likely that baculovirus sensitivity to rodent complement is a result of recognition of elements derived from the insect producer cell membrane or other baculovirus envelope proteins and not specific to the gp64 glycoprotein itself.

To summarize, the findings of the experiments described in the present examples suggest that the gp64 envelope glycoprotein is a useful component of the lentiviral vector system because it confers high transduction efficiency in vitro and in vivo. gp64 is distinctly better than the MLV Ampho envelope protein in its ability to transfer genes to murine cells in vivo and has advantages over the VSV-G envelope in its fortuitous ability to be stably expressed without cytotoxic effects. gp64-pseudotyped lentiviral vectors are also more useful than baculovirus vectors because they are resistant to inactivation by serum complement from animal models such as rodents. Finally, gp64 may be a useful alternative to VSV-G for many applications because it transduces cells in vivo with a similar efficiency but has a more restricted tropism profile, especially with respect to cells of the hematopoietic system including dendritic cells.

Materials and Methods

Cell Culture

The following cell lines were obtained from ATCC and passaged in the specified medium: 293T (CRL-11268), HeLa (CCL-2), HepG2 (HB-8065), K-562 (CCL-243), PC-3 (CRL-1435), U-118 MG (HTB-15), NIH:Ovcar-3 (HTB-161), MOLT-4 (CRL-1582), Hep3B (HB-8064), G-361 (CRL-1424), A549 (CCL-185), Te671 (CRL-8805), HT-1080 (CCL-121), NIH/3T3 (CRL-1658) Cf2Th (CRL-1430), Vero (CCL-81), FO (CRL-1646), KG-1 (CCL-246), SC-1 (CRL-8756), Raji (CCL-86) and XC (CCL-165). C8166 (# 404) and CEM-TART (# 1944) were obtained from the NIH AIDS Research and Reference Reagent Program. HuH7 cells were obtained from Dr. Jing-Hsuing (James) Ou at University of Southern California. HUAEC (#CC-2520) and NHDC (CC-2701) were both obtained from Cambrex (East Rutherford, N.J.) and cultured in the specified Clonetics media. Cells were grown at 37° C. in 5% $CO_2$ at 85% humidity.

In vivo Mouse Studies

All animal work was approved by the Institutional Animal Care and Use Committee at Cell Genesys. 6–8 week old Female NIH Swiss Nude (Taconic, Germantown, N.Y.) mice were cannulated in the hepatic portal vein 1 to 2 days prior to injection. Vectors were injected into the cannula in a total volume of 100 μl. Blood was collected from the retro-orbital plexus at the indicated time points and processed into serum for human Factor IX analysis. For GFP analysis, animals were euthanized 11 days after injection and the medial and left lateral lobes of the liver were collected and processed for GFP analysis as described below.

ELISA Determination of Human Factor IX Concentration

Flat-bottomed 96-well plates (Nunc, Rochester, N.Y.) were coated with 100 μl/well of mouse monoclonal anti-human Factor IX antibody (Roche Applied Science, Indianapolis, Ind.) diluted to 2 μg/ml in BBS (boric acid-buffered saline) and left overnight at 4° C. Following coating the plates were washed with BBS containing 0.025% Tween-20, and blocked with 200 μl/well BBM (1% nonfat milk in BBS) for 2 hr at room temperature. Standards were made using serial dilutions of 20% naïve mouse serum in BBM spiked with human Factor IX (Calbiochem, La Jolla, Calif., 25 ng/ml starting concentration). Mouse serum samples were diluted 1:5 or 1:10 in BBM and 50 μl/well was loaded in duplicate. In 1:10 dilutions, naive mouse serum was added to the dilution to make a final solution of 20% mouse serum in BBM. After a 2-hour incubation at room temperature, the plates were washed and incubated for 90 minutes with 50 μl/well horseradish peroxidase (HRP)-conjugated goat anti-human Factor IX polyclonal antibody (Affinity Biologicals, Ancaster, ON, Canada) that was diluted 1:100 in BBM. After a final wash step, the plates were developed with 50 μl/well o-phenylenediamine dihydrochloride peroxidase substrate (Sigma, St. Louis, Mo.). After 25 minutes, the color reaction was stopped by adding 50 μL/well 2M $H_2SO_4$ and the optical density was determined by reading in a plate reader/spectrophotometer at 490 nm. The limit of detection for the ELISA is approximately 1 ng/ml.

Liver Histology

Livers were processed as previously described for in situ hybridization of mouse embryos (see e.g., Simmons et a., Dev. Biol. (2001) 229:327–333). The medial and left lateral lobes of the mouse livers were analyzed separately. Samples were cyrosectioned at 5–10 μm and directly visualized for GFP fluorescence using a Zeiss Axioplan microscope (Carl Zeizz, Thornwood, N.Y.).

Determination of Complement Sensitivity

Serum samples from single human donors, Nude rats or pooled sera from C57BL/6 mice were thawed and half of each serum sample was heated at 56° C. for 1 hr to inactivate the complement. All sera were made by collecting fresh whole blood and allowing it to clot completely for several hours. Clots were pelleted by centrifugation and the serum supernatants were removed and frozen immediately in aliquots. CMV-GFP vector samples with different envelope pseudotypes were diluted to $10^6$ TU/ml. 30–75 μl of the vector was diluted 1:5 into normal or heat-inactivated serum (or medium containing 10% heat-inactivated FBS as the no-serum control) and the mixture was incubated at 37° C. for 1 hour. Following the incubation, medium was added to the reaction for an additional 1:5 dilution and then serially diluted twice at a 1:10 ratio and used to infect 293T cells in the presence of 8 μg/ml Polybrene for end point titer determination. The titer value was divided by the titer determined for the vector mixed with medium (the no-serum control) and reported as the % recovery of titer compared to this control. All serum samples were analyzed for hemolytic complement activity ($CH_{50}$) using kits from Quidel ($CH_{50}$ Eq Enzyme Immunoassay; San Diego, Calif.) or Diamedix (E-Z $CH_{50}$; Miami, Fla.).

TABLE 1

293T Cells are Stably Transduced (not pseudotransduced) by VSV-G and gp64-pseudotyped Lentiviral Vectors

| Vector | | % GFP-Positive Cells | | Mean Fluorescence | |
|---|---|---|---|---|---|
| Envelope | Dilution | Day 3 | Day 17 | Day 3 | Day 17 |
| VSVG | 1:25 | 12.00 | 8.98 | 630 | 1180 |
|  | 1:250 | 1.89 | 1.31 | 567 | 1253 |
| gp64 | 1:25 | 3.68 | 3.39 | 587 | 1565 |
|  | 1:250 | 0.53 | 0.53 | 492 | 1323 |

TABLE 2

Gp64-pseudotyped Lentiviral Vectors Survive Concentration by Ultracentrifugation with Excellent Recovery of Titer & p24

| Envelope | Pre-Concentration p24 (ng/ml) | Pre-Concentration Titer/293T | Post-Concentration p24 (ug/ml) | Post-Concentration Titer/293T | % Recovery p24 | % Recovery Titer | Fold-Concentration |
|---|---|---|---|---|---|---|---|
| VSVG | 276.3 | $8.96 \times 10^6$ | 17.72 | $8.90 \times 10^8$ | 64.10% | 99.30% | 100 |
|  | 123.5 | $9.17 \times 10^6$ | 134.90 | $6.94 \times 10^9$ | 109.30% | 75.68% | 1000 |
| gp64 | 32.5 | $1.14 \times 10^5$ | 3.20 | $1.38 \times 10^7$ | 98.50% | 121.00% | 100 |
|  | 11.7 | $1.38 \times 10^5$ | 7.74 | $7.43 \times 10^7$ | 66.20% | 60.60% | 888 |

What is claimed is:

1. A retroviral packaging cell comprising:
   (a) a first nucleotide sequence comprising a gag, a pol, or gag and pol genes; and
   (b) a second nucleotide sequence comprising a baculoviral envelope gene.

2. The packaging cell of claim 1, wherein the baculoviral envelope gene comprises a gp64 envelope gene.

3. The packaging cell of claim 1, wherein the envelope gene is from *Autographa californica* nucleopolyhedrovirus, *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, *Dhori virus,* Thogoto virus, *Antheraea pernyi* nucleopolyhedrovirus or Batken virus.

4. The packaging cell of claim 1, wherein the retroviral packaging cell is a lentiviral packaging cell.

5. A retroviral producer cell comprising the packaging cell of claim 1 and a retroviral transfer vector.

6. A method of producing a retroviral producer cell comprising transforming a packaging cell of claim 1 with a retroviral transfer vector.

7. The packaging cell of claim 4, wherein the lentiviral packaging cell is a human immunodeficiency virus (HIV) packaging cell.

8. The packaging cell of claim 4, which lacks a functional tat gene.

9. The packaging cell of claim 4, further comprising a third nucleotide sequence that comprises a rev gene.

10. The packaging cell of claim 4, which lacks functional genes selected from vif, vpr, vpu, vpx and nef, or a combination thereof.

11. The packaging cell of claim 7, wherein the HIV is HIV-1.

12. The producer cell of claim 5, which produces a titer of retroviral particles of at least about $1 \times 10^5$ infectious units per ml.

13. The producer cell of claim 5, which produces a titer of retroviral particles of at least about $5 \times 10^5$ infectious units per ml.

14. The producer cell of claim 5, which produces a titer of retroviral particles of at least about $5 \times 10^6$ infectious units per ml.

15. A method of producing a recombinant retroviral vector comprising culturing a producer cell of claim 5 in a medium and recovering recombinant retroviral particles from the medium.

16. A method of delivering a transgene to a cell comprising contacting the cell with recombinant retroviral particles produced by the producer cell of claim 5 under conditions permitting transduction of the cell with a retroviral particle.

17. A set of retroviral vectors comprising:
   (a) in a first vector, a first nucleotide sequence comprising a gag, a pol, or gag and pol genes operably linked to an expression control sequence; and
   (b) in a second vector, a second nucleotide sequence comprising a baculoviral envelope gene operably linked to an expression control sequence.

18. The set of claim 17, wherein the baculoviral envelope gene comprises a gp64 envelope gene.

19. The set of claim 17, wherein the envelope gene is derived from *Autographa californica* nucleopolyhedrovirus, *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, *Dhori virus,* Thogoto virus, *Antheraea pernyi* nucleopolyhedrovirus or Batken virus.

20. The set of claim 17, wherein the retroviral vectors are lentiviral vectors.

21. A method of producing a retroviral packaging cell comprising transforming a cell with the set of vectors of claim 17.

22. The set of claim 20, wherein the lentiviral vectors are HIV vectors.

23. The set of claim 20, which lacks a functional tat gene.

24. The set of claim 20, further comprising a third nucleotide sequence that comprises a rev gene.

25. The set of claim 20, which lacks functional genes selected from vif, vpr, vpu, vpx and nef, or a combination thereof.

26. The set of claim 22, wherein the HIV is HIV-1.

* * * * *